(12) United States Patent
DellaPenna et al.

(10) Patent No.: US 6,232,530 B1
(45) Date of Patent: May 15, 2001

(54) MARIGOLD DNA ENCODING BETA-CYCLASE

(75) Inventors: Dean DellaPenna, Reno, NV (US); Francis X. Cunningham, Jr., Chevy Chase, MD (US)

(73) Assignees: University of Nevada, Reno, NV (US); University of Maryland, College Park, MD (US)

( * ) Notice: Subject to any disclaimer, the term of this patent is extended or adjusted under 35 U.S.C. 154(b) by 0 days.

(21) Appl. No.: 09/201,641

(22) Filed: Nov. 30, 1998

(51) Int. Cl.⁷ .............................. A01H 5/00; C12N 15/82
(52) U.S. Cl. ..................... 800/282; 536/23.2; 536/23.6
(58) Field of Search ........................... 435/69.1, 320.1, 435/419, 468; 536/23.2, 23.6; 800/278, 282, 286, 287, 298

(56) References Cited

U.S. PATENT DOCUMENTS

| | | |
|---|---|---|
| 5,320,961 | 6/1994 | Zhong et al. . |
| 5,429,939 | 7/1995 | Misawa et al. . |
| 5,530,188 | 6/1996 | Ausich et al. . |
| 5,618,988 | 4/1997 | Hauptmann et al. . |
| 5,684,238 | 11/1997 | Ausich et al. . |
| 5,736,369 | 4/1998 | Bowen et al. . |
| 5,744,341 | 4/1998 | Cunningham, Jr. et al. . |
| 5,750,865 | 5/1998 | Bird et al. . |
| 5,767,368 | 6/1998 | Zhong et al. . |

FOREIGN PATENT DOCUMENTS

| | | |
|---|---|---|
| WO9602594A2 | 1/1996 | (WO) . |
| WO96/28014 | 9/1996 | (WO) . |
| WO96/36717 | 11/1996 | (WO) . |
| WO 97/36998 | 10/1997 | (WO) . |
| WO 98/06862 | 2/1998 | (WO) . |
| WO 99/61652 | 12/1999 | (WO) . |
| WO 99/63055 | 12/1999 | (WO) . |

OTHER PUBLICATIONS

Stam M, et al. "The silence of genes in transgenic plants." Ann. Bot. 79: 3–12, 1997.*
Koziel MG, et al. "Optimizing expression of transgenes with an emphasis on post–transcriptional events." Plant Mol. Biol. 32: 393–405, 1996.*
Smith CJS, et al. "Antisense RNA inhibition of polygalacturonase gene expression in transgenic tomatoes." Nature 334: 724–726, Aug. 25, 1988.*
Gomez, Rev. Espanola De Fisiol. 34: 253–256 (1978).
Sun, J. Biol. Chem. 271: 24349–24352 (1996).
Cunningham, Annu. Rev. Plant Physiol. Plant Mol. Biol. 49: 557–581 (1998).
Cunningham, F.X.,Jr., The Plant Cell, vol. 8, 1613–1626, Sep. 1996.
Hirschberg, J., Pure & Appl. Chem. vol. 69, No. 10, pp. 2151–2158 (1997).
Bird, C.R., Bio/Technology vol. 9, 635–639 Jul. 1991.
Kothari, S.L., J. Plant Physiol. vol. 122, 235–241 (1986).
Frey, et al., Plant J., vol. 8:693–701 (1995).
Misawa, et al., Plant J. vol. 6:481–489 (1994).
Senior, Biotechnol. Genet. Rev., 15:79–119 (1998).
Nellen, et al., Mol. Biotechnol., 6:7–15 (1996).
Yamaguchi–Shinozaki, et al., Plant Cell 6:251–264 (1994).
Zhong, et al., Plant Physiology, 110:1097–1107 (1996).
Zhang, et al., Theor. Appl. Genet., 92:752–761 (1996).
Zhong, et al., Planta, 187:483–489 (1992).

* cited by examiner

*Primary Examiner*—Amy J. Nelson
(74) *Attorney, Agent, or Firm*—Ian C. McLeod

(57) ABSTRACT

The present invention describes the gene encoding beta-cyclase from marigolds. In particular, the present invention provides the DNA sequence for the gene encoding marigold beta-cyclase as well as vectors containing the same and bacteria and plants transformed with the vectors.

20 Claims, 6 Drawing Sheets

Marigold beta cyclase cDNA sequence

TCTAGAACTAGTGGATCCCCCGGGCTGCAGGAATTCGGCACGAGACTTCCCATTATCC
AATCTCTCAAAACCATCAACAATTTCACCACATCATTTACCGGTAAGTCTTCATATCTTT
CAATTCTTCACAAACCCACTTCAATTCTCATCATTAATCTCATAAAGTTCATACCTTTGTT
GTCAATTTTGGTGTTTCTTGGGTTCTTGATTCATAAAGTTCATAACTTTGTTGCTGTTTTT
GTGTTTCTTGATTCATAAAGTTCAAAACTTTGTTGGTTTTTTTGTTAAATTACATCTGGG
TTTCATGGATACCTTCTTAAGAACATACAATTCGTTTGAATTTGTGCACCCAAGTAACAA
ATTTGCAGGAAATTTGAACAATTTGAATCAATTGAATCAATCAAAGTCTCAATTTCAAG
ACTTTAGATTTGGCCCAAAAAAATCCCAATTCAAATTAGGGCAAAAATATTGTGTTAAA
GCTAGTAGTAGTGCTTTGTTAGAACTTGTTCCTGAAATCAAGAAAGAAATCTTGATTT
TGATCTTCCTATGTATGATCCATCAAGAAATGTTGTGGTGGATCTTGTGGTGGTTGGTG
GTGGTCCTTCAGGGTTAGCAGTGGCTCAACAAGTGTCTGAGGCTGGTCTCACAGTGTG
CTCAATTGACCCATCACCTAAACTCATTTGGCCCAATAATTATGGTGTTTGGGTTGATG
AGTTTGAAGCTATGGATTTGTTGGATTGTTTGGATACAACTTGGTCAAGTGCTGTTGTT
TACATTGATGAAAAGTCAACCAAGAGTCTTAATAGACCATATGCAAGAGTCAATAGAA
AACAACTTAAAACAAAGATGTTACAAAAGTGTATAGCAAATGGGGTTAAGTTTCATCAA
GCAAAAGTCATCAAAGTGATTCATGAAGAGTTAAAATCTTTGTTGATTTGTAATGATGG
TGTCACAATTCAAGCCACTTTGGTTCTTGATGCAACTGGTTTTTCAAGATCTTTAGTTCA
ATATGATAAGCCTTATAACCCTGGGTACCAAGTGGCTTATGGGATTTTAGCCGAAGTT
GAAGAACACCCTTTTGACGTTGATAAAATGTTGTTTATGGATTGGAGAGATTCACACCT
TGATCAAAATCTTGAAATTAAAGCTAGAAATTCAAGAATCCCAACTTTTTTATACGCGAT
GCCATTTTCGTCTACAAGAATCTTTCTTGAAGAAACATCACTCGTTGCTCGTCCGGGGT
TGAAGATGGAAGATATTCAAGAAAGAATGGCTTACAGGCTAAAGCATTTGGGGATAAA
AGTAAAAAGCATTGAAGAAGACGAACGTTGTGTTATCCCGATGGGCGGGCCCCTACC
AGTGCTCCCTCAACGGGTTCTTGGAATAGGTGGTACAGCAGGAATGGTGCATCCGTCA
ACCGGATACATGGTGGCAAGAACGCTAGCAGCCGCCCCGATTGTTGCAAAGTCAATA
ATCCGGTATCTTAATAACGAAAAAAGTATGGTGGCCGACGTCACCGGAGATGATTTAG
CAGCCGGAATATGGAGAGAATTGTGGCCTATTGAAAGAAGGAGACAAAGGGAGTTTT
TTTGTTTTGGGATGGATATATTGTTGAAGCTTGATTTGGAAGGTACTAGAAGGTTCTTT
GATGCGTTTTTCGACTTGGAACCTCGTTATTGGCATGGGTTTTTGTCGTCGAGGTTGTT
TCTACCGGAGTTAGTGACGTTTGGGCTATCGCTTTTCGGTCATGCTTCGAATACTTGTA
GAGTTGAAATTATGGCAAAAGGGACTCTTCCATTGGCAACTATGATTGGTAATTTGGTT
AGAGATCGAGAATGAATAATTGAATATCAAGATTAATTTATAGTTATTTATATATACTTG
TATGCTTTCAGTTTTTGTTAATTGGATGTTATGGTAATTGTATGTTTTAAGTTGATTAAA
AAAAAAAAAAAAAAA

FIG. 3

Marigold beta cyclase protein sequence

MDTFLRTYNSFEFVHPSNKFAGNLNNLNQLNQSKSQFQDFRFGPKKSQFKLGQKYCVK
ASSSALLELVPEIKKENLDFDLPMYDPSRNVVVDLVVVGGGPSGLAVAQQVSEAGLTVCSI
DPSPKLIWPNNYGVWVDEFEAMDLLDCLDTTWSSAVVYIDEKSTKSLNRPYARVNRKQL
KTKMLQKCIANGVKFHQAKVIKVIHEELKSLLICNDGVTIQATLVLDATGFSRSLVQYDKP
YNPGYQVAYGILAEVEEHPFDVDKMLFMDWRDSHLDQNLEIKARNSRIPTFLYAMPFSST
RIFLEETSLVARPGLKMEDIQERMAYRLKHLGIKVKSIEEDERCVIPMGGPLPVLPQRVLGI
GGTAGMVHPSTGYMVARTLAAAPIVAKSIIRYLNNEKSMVADVTGDDLAAGIWRELWPIE
RRRQREFFCFGMDILLKLDLEGTRRFFDAFFDLEPRYWHGFLSSRLFLPELVTFGLSLFGH
ASNTCRVEIMAKGTLPLATMIGNLVRDRE

FIG. 4

Marigold epsilon cyclase cDNA sequence

```
GGCACGAGGCAAAGCAAAGGTTGTTTGTTGTTGTTGTTGAGAGACACTCCAATCCAAA
CAGATACAAGGCGTGACTGGATATTTCTCTCTCGTTCCTAACAACAGCAACGAAGAAG
AAAAAGAATCATTACTAACAATCAATGAGTATGAGAGCTGGACACATGACGGCAACAA
TGGCGGCTTTTACATGCCCTAGGTTTATGACTAGCATCAGATACACGAAGCAAATTAA
GTGCAACGCTGCTAAAAGCCAGCTAGTCGTTAAACAAGAGATTGAGGAGGAAGAAGA
TTATGTGAAAGCCGGTGGATCGGAGCTGCTTTTTGTTCAAATGCAACAGAATAAGTCC
ATGGATGCACAGTCTAGCCTATCCCAAAAGCTCCCAAGGGTACCAATAGGAGGAGGA
GGAGACAGTAACTGTATACTGGATTTGGTTGTAATTGGTTGTGGTCCTGCTGGCCTTG
CTCTTGCTGGAGAATCAGCCAAGCTAGGCTTGAATGTCGCACTTATCGGCCCTGATCT
TCCTTTTACAAATAACTATGGTGTTTGGGAGGATGAATTTATAGGTCTTGGACTTGAGG
GCTGTATTGAACATGTTTGGCGAGATACTGTAGTATATCTTGATGACAACGATCCCATT
CTCATAGGTCGTGCCTATGGACGAGTTAGTCGTGATTTACTTCACGAGGAGTTGTTGA
CTAGGTGCATGGAGTCAGGCGTTTCATATCTGAGCTCCAAAGTGGAACGGATTACTGA
AGCTCCAAATGGCCTAAGTCTCATAGAGTGTGAAGGCAATATCACAATTCCATGCAGG
CTTGCTACTGTCGCTTCTGGAGCAGCTTCTGGAAAACTTTTGCAGTATGAACTTGGCG
GTCCCCGTGTTTGCGTTCAAACAGCTTATGGTATAGAGGTTGAGGTTGAAAGCATACC
CTATGATCCAAGCCTAATGGTTTTCATGGATTATAGAGACTACACCAAACATAAATCTC
AATCACTAGAAGCACAATATCCAACATTTTTGTATGTCATGCCAATGTCTCCAACTAAA
GTATTCTTTGAGGAAACTTGTTTGGCTTCAAAAGAGGCCATGCCTTTTGAGTTATTGAA
GACAAAACTCATGTCAAGATTAAAGACTATGGGGATCCGAATAACCAAAACTTATGAA
GAGGAATGGTCATATATTCCAGTAGGTGGATCCTTACCAAATACCGAGCAAAAGAACC
TTGCATTTGGTGCTGCTGCTAGCATGGTGCATCCAGCCACAGGATATTCGGTTGTAAG
ATCACTGTCAGAAGCTCCTAATTATGCAGCAGTAATTGCAAAGATTTTAGGGAAAGGA
AATTCAAAACAGATGCTTGATCATGGAAGATACACAACCAACATCTCAAAGCAAGCTT
GGGAAACACTTTGGCCCCTTGAAAGGAAAAGACAGAGAGCATTCTTTCTCTTTGGATT
AGCACTGATTGTCCAGATGGATATTGAGGGGACCCGCACATTCTTCCGGACTTTCTTC
CGCTTGCCCACATGGATGTGGTGGGGGTTTCTTGGATCTTCGTTATCATCAACTGACTT
GATAATATTTGCGTTTTACATGTTTATCATAGCACCGCATAGCCTGAGAATGGGTCTGG
TTAGACATTTGCTTTCTGACCCGACAGGAGGAACAATGTTAAAAGCGTATCTCACGATA
TAAATAACTCTAGTCGCGATCAGTTTAGATTATAGGCACATCTTGCATATATATGTAT
AAACCTTATGTGTGCTGTATCCTTACATCAACACAGTCATTAATTGTATTTCTTGGGGTA
ATGCTGATGAAGTATTTTCTGGAAAAAAAAAAAAAAAAAAAACTCGAGACTAGTTCACTCT
CTCTCTCCTCGTGCCGATTC
```

FIG. 5

Marigold epsilon cyclase protein sequence

```
MSMRAGHMTATMAAFTCPRFMTSIRYTKQIKCNAAKSQLVVKQEIEEEEDYVKAGGSELL
FVQMQQNKSMDAQSSLSQKLPRVPIGGGGDSNCILDLVVIGCPAGLALAGESAKLGLNV
ALIGPDLPFTNNYGVWEDEFIGLGLEGCIEHVWRDTVVYLDDNDPILIGRAYGRVSRDLLH
EELLTRCMESGVSYLSSKVERITEAPNGLSLIECEGNITIPCRLATVASGAASGKLLQYELG
GPRVCVQTAYGIEVEVESIPYDPSLMVFMDYRDYTKHKSQSLEAQYPTFLYVMPMSPTKV
FFEETCLASKEAMPFELLKTKLMSRLKTMGIRITKTYEEEWSYIPVGGSLPNTEQKNLAFG
AAASMVHPATGYSVVRSLSEAPNYAAVIAKILGKGNSKQMLDHGRYTTNISKQAWETLW
PLERKRQRAFFLFGLALIVQMDIEGTRTFFRTFFRLPTWMWWGFLGSSLSSTDLIIFAFYMF
IIAPHSLRMGLVRHLLSDPTGGTMLKAYLTI
```

FIG. 6

Marigold Beta Hydroxylase DNA sequence
GGCACGAGATTGCTGTCCCTTGTAGCTCAAGACCATTTGGCTTAGGTCGAATGCGGTT
ACTTGGTCATAAACCCACAACCATAACTTGTCACTTCCCCTTTTCTTTTTCTATCAAATC
ATTTACCCCAATTGTTAGGGGCAGAAGATGTACTGTTTGTTTTGTTGCCGGTGGCGAC
AGTAATAGTAACAGTAATAATAATAGTGACAGTAATAGTAATAATCCGGGTCTGGATTT
AAACCCGGCGGTTATGAACCGTAACCGTTTGGTTGAAGAAAAAATGGAGAGGAAAAA
ATCGGAACGATTTACTTATCTTGTTGCAGCTATTATGTCTACTTTTGGAATTACTTCAAT
GGCGGTTATGGCGGTTTATTACCGGTTTTCATGGCAAATGGAGGGTGGAGAAATTCCT
TATGTGGAGATGTTTGGTACATTTGCTCTCTCCGTTGGTGCTGCGGTAGGAATGGAGT
ATTGGGCAAGATGGGCTCATGAGGCACTATGGCATGCTTCTTTGTGGCACATGCATGA
GTCACACCATAAGCCACGAGAAGGTCCGTTTGAGCTTAATGATGTGTTTGCTATAACA
AATGCGGTCCCGGCCATTGCGTTGCTTAGTTATGGGTTTTTCCACAAAGGCATAATTCC
GGGTCTTTGTTTTGGGGCGGGACTGGGAATTACGGTGTTTGGAATGGCGTATATGTTC
GTCCACGACGGGCTAGTTCACAGAAGATTCCAAGTGGGTCCGATTGCGAATGTTCCCT
ATCTTCGAAGGGTTGCAGCGGCTCATCAGCTGCATCACACGGAAAAATTTAATGGTGT
TCCTTATGGCTTGTTCTTGGGACCTAAGGAGCTAGAAGAAGTGGGTGGTACGGAAGA
ATTGGACAAGGAGATTCAAAGAAGAATTAAATTGTATAATAATACTAAATAAATAAATT
TTGTATAAAATTAATATAATTTAATGATATCTTTTTGTTTTAAAAAAAAAAAAAAAAA

FIG. 7

Marigold Beta Hydroxylase protein sequence
MRLLGHKPTTITCHFPFSFSIKSFTPIVRGRRCTVCFVAGGDSNSNSNNNSDSNSNNPGL
DLNPAVMNRNRLVEEKMERKKSERFTYLVAAIMSTFGITSMAVMAVYYRFSWQMEGGEI
PYVEMFGTFALSVGAAVGMEYWARWAHEALWHASLWHMHESHHKPREGPFELNDVFA
ITNAVPAIALLSYGFFHKGIIPGLCFGAGLGITVFGMAYMFVHDGLVHRRFQVGPIANVPY
LRRVAAAHQLHHTEKFNGVPYGLFLGPKELEEVGGTEELDKEIQRRIKLYNNTK

FIG. 8

Marigold IPP Isomerase cDNA sequence (start codon in bold)
CAGGAATTCGGCACGAGCTCAATCTCAATCAACCCTCTTCTTCTCTCCCAGTATCTATA
CCAAAAACAACTCAAATCTCCTCCGTCGCTCTTACTCCGCCATGGGTGACGACTCCGG
CATGGATGCTGTTCAGCGACGTCTCATGTTTAACGATGAATGCATTTTGGTGGATGAG
TGTGACAATGTGGTGGGACATGATACCAAATACAATTGTCACTTGATGGAGAAGATTG
AAACAGGTAAAATGCTGCACAGAGCATTCAGCGTTTTCTATTCAATTCAAAATACGAG
TTACTTCTTCAGCAACGGTCTGCAACCAAGGTGACATTTCCTTTAGTATGGACCAACAC
CTGTTGCAGCCATCCACTCTACAGAGAATCCGAGCTTGTTCCCGAAAACGCCCTTGGA
GTAAGAAATGCTGCACAGAGGAAGCTGTTGGATGAACTCGGTATCCCTGCTGAAGAT
GTTCCCGTTGATCAGTTTACTCCTTTAGGTCGCATGCTCTACAAGGCTCCATCTGATGG
AAAGTGGGGAGAACATGAACTTGACTACCTACTTTTCATAGTGAGAGACGTTGCTGTA
AACCCGAACCCAGATGAAGTGGCGGATATCAAATATGTGAACCAAGAAGAGTTAAAG
GAGCTGCTAAGGAAAGCAGATGCGGGGGAGGAGGGTTTGAAGCTGTCTCCATGGTTC
AGGTTAGTGGTTGATAACTTCTTGTTCAAGTGGTGGGATCATGTGCAAAAGGTTACAC
TCACTGAAGCAATTGATATGAAAACCATACACAAGCTGATATAGAAACACACCCTCAAC
CGAAAAGTTCAAGCCTAATAATTCGGGTTGGGTCGGGTCTACCATCAATTGTTTTTTTC
TTTTAAGAAGTTTTAATCTCTATTTGAGCATGTTGATTCTTGTCTTTTGTGTGTAAGATTT
TGGGTTTCGTTTCAGTTGTAATAATGAACCATTGATGGTTTGCAATTTCAAGTTCCTATC
GACAAAAAAAAAAAAAAAAAAAACTC

FIG. 9

Marigold IPP Isomerase protein sequence
MGDDSGMDAVQRRLMFNDECILVDECDNVVGHDTKYNCHLMEKIETGKMLHRAFSVFL
FNSKYELLLQQRSATKVTFPLVWTNTCCSHPLYRESELVPENALGVRNAAQRKLLDELGIP
AEDVPVDQFTPLGRMLYKAPSDGKWGEHELDYLLFIVRDVAVNPNPDEVADIKYVNQEEL
KELLRKADAGEEGLKLSPWFRLVVDNFLFKWWDHVQKVTLTEAIDMKTIHKLI

FIG. 10

SEQUENCE LISTING

<160> NUMBER OF SEQ ID NOS: 8

<210> SEQ ID NO: 1
<211> LENGTH: 1959
<212> TYPE: DNA
<213> ORGANISM: Tagetes erecta
<220> FEATURE:
<221> NAME/KEY: CDS
<222> LOCATION: (304)..(1836)
<223> OTHER INFORMATION: beta-cyclase

<400> SEQUENCE: 1
tctagaacta gtggatcccc cgggctgcag gaattcggca cgagacttcc cattatccaa    60

-continued

```
tctctcaaaa ccatcaacaa tttcaccaca tcatttaccg gtaagtcttc atatctttca      120
attcttcaca aacccacttc aattctcatc attaatctca taaagttcat acctttgttg      180
tcaattttgg tgtttcttgg gttcttgatt cataaagttc ataactttgt tgctgttttt      240
gtgtttcttg attcataaag ttcaaaattt gttggttttt ttgttaaatt acatctgggt      300 ttc atg gat acc ttc tta aga aca tac aat tcg ttt gaa ttt gtg cac       348
    Met Asp Thr Phe Leu Arg Thr Tyr Asn Ser Phe Glu Phe Val His
    1               5                  10                  15 cca agt aac aaa ttt gca gga aat ttg aac aat ttg aat caa ttg aat       396
Pro Ser Asn Lys Phe Ala Gly Asn Leu Asn Asn Leu Asn Gln Leu Asn
                20                  25                  30 caa tca aag tct caa ttt caa gac ttt aga ttt ggc cca aaa aaa tcc       444
Gln Ser Lys Ser Gln Phe Gln Asp Phe Arg Phe Gly Pro Lys Lys Ser
            35                  40                  45 caa ttc aaa tta ggg caa aaa tat tgt gtt aaa gct agt agt agt gct       492
Gln Phe Lys Leu Gly Gln Lys Tyr Cys Val Lys Ala Ser Ser Ser Ala
        50                  55                  60 ttg tta gaa ctt gtt cct gaa atc aag aaa gaa aat ctt gat ttt gat       540
Leu Leu Glu Leu Val Pro Glu Ile Lys Lys Glu Asn Leu Asp Phe Asp
    65                  70                  75 ctt cct atg tat gat cca tca aga aat gtt gtg gtg gat ctg gtg gtg       588
Leu Pro Met Tyr Asp Pro Ser Arg Asn Val Val Val Asp Leu Val Val
80                  85                  90                  95 gtt ggt ggt ggt cct tca ggg tta gca gtg gct caa caa gtg tct gag       636
Val Gly Gly Gly Pro Ser Gly Leu Ala Val Ala Gln Gln Val Ser Glu
                100                 105                 110 gct ggt ctc aca gtg tgc tca att gac cca tca cct aaa ctc att tgg       684
Ala Gly Leu Thr Val Cys Ser Ile Asp Pro Ser Pro Lys Leu Ile Trp
            115                 120                 125 ccc aat aat tat ggt gtt tgg gtt gat gag ttt gaa gct atg gat ttg       732
Pro Asn Asn Tyr Gly Val Trp Val Asp Glu Phe Glu Ala Met Asp Leu
        130                 135                 140 ttg gat tgt ttg gat aca act tgg tca agt gct gtt gtt tac att gat       780
Leu Asp Cys Leu Asp Thr Thr Trp Ser Ser Ala Val Val Tyr Ile Asp
    145                 150                 155 gaa aag tca acc aag agt ctt aat aga cca tat gca aga gtc aat aga       828
Glu Lys Ser Thr Lys Ser Leu Asn Arg Pro Tyr Ala Arg Val Asn Arg
160                 165                 170                 175 aaa caa ctt aaa aca aag atg tta caa aag tgt ata gca aat ggg gtt       876
Lys Gln Leu Lys Thr Lys Met Leu Gln Lys Cys Ile Ala Asn Gly Val
                180                 185                 190 aag ttt cat caa gca aaa gtc atc aaa gtg att cat gaa gag tta aaa       924
Lys Phe His Gln Ala Lys Val Ile Lys Val Ile His Glu Glu Leu Lys
            195                 200                 205 tct ttg ttg att tgt aat gat ggt gtc aca att caa gcc act ttg gtt       972
Ser Leu Leu Ile Cys Asn Asp Gly Val Thr Ile Gln Ala Thr Leu Val
        210                 215                 220 ctt gat gca act ggt ttt tca aga tct tta gtt caa tat gat aag cct      1020
Leu Asp Ala Thr Gly Phe Ser Arg Ser Leu Val Gln Tyr Asp Lys Pro
    225                 230                 235 tat aac cct ggg tac caa gtg gct tat ggg att tta gcc gaa gtt gaa      1068
Tyr Asn Pro Gly Tyr Gln Val Ala Tyr Gly Ile Leu Ala Glu Val Glu
240                 245                 250                 255 gaa cac cct ttt gac gtt gat aaa atg ttg ttt atg gat tgg aga gat      1116
Glu His Pro Phe Asp Val Asp Lys Met Leu Phe Met Asp Trp Arg Asp
                260                 265                 270 tca cac ctt gat caa aat ctt gaa att aaa gct aga aat tca aga atc      1164
Ser His Leu Asp Gln Asn Leu Glu Ile Lys Ala Arg Asn Ser Arg Ile
            275                 280                 285
```

```
cca act ttt tta tac gcg atg cca ttt tcg tct aca aga atc ttt ctt    1212
Pro Thr Phe Leu Tyr Ala Met Pro Phe Ser Ser Thr Arg Ile Phe Leu
        290                 295                 300 gaa gaa aca tca ctc gtt gct cgt ccg ggg ttg aag atg gaa gat att    1260
Glu Glu Thr Ser Leu Val Ala Arg Pro Gly Leu Lys Met Glu Asp Ile
305                 310                 315 caa gaa aga atg gct tac agg cta aag cat ttg ggg ata aaa gta aaa    1308
Gln Glu Arg Met Ala Tyr Arg Leu Lys His Leu Gly Ile Lys Val Lys
320                 325                 330                 335 agc att gaa gaa gac gaa cgt tgt gtt atc ccg atg ggc ggg ccc cta    1356
Ser Ile Glu Glu Asp Glu Arg Cys Val Ile Pro Met Gly Gly Pro Leu
                340                 345                 350 cca gtg ctc cct caa cgg gtt ctt gga ata ggt ggt aca gca gga atg    1404
Pro Val Leu Pro Gln Arg Val Leu Gly Ile Gly Gly Thr Ala Gly Met
        355                 360                 365 gtg cat ccg tca acc gga tac atg gtg gca aga acg cta gca gcc gcc    1452
Val His Pro Ser Thr Gly Tyr Met Val Ala Arg Thr Leu Ala Ala Ala
        370                 375                 380 ccg att gtt gca aag tca ata atc cgg tat ctt aat aac gaa aaa agt    1500
Pro Ile Val Ala Lys Ser Ile Ile Arg Tyr Leu Asn Asn Glu Lys Ser
385                 390                 395 atg gtg gcc gac gtc acc gga gat gat tta gca gcc gga ata tgg aga    1548
Met Val Ala Asp Val Thr Gly Asp Asp Leu Ala Ala Gly Ile Trp Arg
400                 405                 410                 415 gaa ttg tgg cct att gaa aga agg aga caa agg gag ttt ttt tgt ttt    1596
Glu Leu Trp Pro Ile Glu Arg Arg Arg Gln Arg Glu Phe Phe Cys Phe
                420                 425                 430 ggg atg gat ata ttg ttg aag ctt gat ttg gaa ggt act aga agg ttc    1644
Gly Met Asp Ile Leu Leu Lys Leu Asp Leu Glu Gly Thr Arg Arg Phe
        435                 440                 445 ttt gat gcg ttt ttc gac ttg gaa cct cgt tat tgg cat ggg ttt ttg    1692
Phe Asp Ala Phe Phe Asp Leu Glu Pro Arg Tyr Trp His Gly Phe Leu
        450                 455                 460 tcg tcg agg ttg ttt cta ccg gag tta gtg acg ttt ggg cta tcg ctt    1740
Ser Ser Arg Leu Phe Leu Pro Glu Leu Val Thr Phe Gly Leu Ser Leu
465                 470                 475 ttc ggt cat cgt tcg aat act tgt aga gtt gaa att atg gca aaa ggg    1788
Phe Gly His Arg Ser Asn Thr Cys Arg Val Glu Ile Met Ala Lys Gly
480                 485                 490                 495 act ctt cca ttg gca act atg att ggt aat ttg gtt aga gat cga gaa    1836
Thr Leu Pro Leu Ala Thr Met Ile Gly Asn Leu Val Arg Asp Arg Glu
                500                 505                 510 tgaataattg aatatcaaga ttaatttata gttatttata tatacttgta tgctttcagt    1896
ttttgttaat tggatgttat ggtaattgta tgttttaagt tgattaaaaa aaaaaaaaaa    1956
aaa                                                                 1959

<210> SEQ ID NO: 2
<211> LENGTH: 511
<212> TYPE: PRT
<213> ORGANISM: Tagetes erecta

<400> SEQUENCE: 2

Met Asp Thr Phe Leu Arg Thr Tyr Asn Ser Phe Glu Phe Val His Pro
 1               5                  10                  15

Ser Asn Lys Phe Ala Gly Asn Leu Asn Asn Leu Asn Gln Leu Asn Gln
                20                  25                  30

Ser Lys Ser Gln Phe Gln Asp Phe Arg Phe Gly Pro Lys Lys Ser Gln
        35                  40                  45
```

```
Phe Lys Leu Gly Gln Lys Tyr Cys Val Lys Ala Ser Ser Ser Ala Leu
     50                  55                  60

Leu Glu Leu Val Pro Glu Ile Lys Lys Glu Asn Leu Asp Phe Asp Leu
 65                  70                  75                  80

Pro Met Tyr Asp Pro Ser Arg Asn Val Val Asp Leu Val Val
                 85                  90                  95

Gly Gly Gly Pro Ser Gly Leu Ala Val Ala Gln Gln Val Ser Glu Ala
                100                 105                 110

Gly Leu Thr Val Cys Ser Ile Asp Pro Ser Pro Lys Leu Ile Trp Pro
                115                 120                 125

Asn Asn Tyr Gly Val Trp Val Asp Glu Phe Glu Ala Met Asp Leu Leu
    130                 135                 140

Asp Cys Leu Asp Thr Thr Trp Ser Ser Ala Val Val Tyr Ile Asp Glu
145                 150                 155                 160

Lys Ser Thr Lys Ser Leu Asn Arg Pro Tyr Ala Arg Val Asn Arg Lys
                165                 170                 175

Gln Leu Lys Thr Lys Met Leu Gln Lys Cys Ile Ala Asn Gly Val Lys
                180                 185                 190

Phe His Gln Ala Lys Val Ile Lys Val Ile His Glu Glu Leu Lys Ser
        195                 200                 205

Leu Leu Ile Cys Asn Asp Gly Val Thr Ile Gln Ala Thr Leu Val Leu
    210                 215                 220

Asp Ala Thr Gly Phe Ser Arg Ser Leu Val Gln Tyr Asp Lys Pro Tyr
225                 230                 235                 240

Asn Pro Gly Tyr Gln Val Ala Tyr Gly Ile Leu Ala Glu Val Glu Glu
                245                 250                 255

His Pro Phe Asp Val Asp Lys Met Leu Phe Met Asp Trp Arg Asp Ser
                260                 265                 270

His Leu Asp Gln Asn Leu Glu Ile Lys Ala Arg Asn Ser Arg Ile Pro
        275                 280                 285

Thr Phe Leu Tyr Ala Met Pro Phe Ser Ser Thr Arg Ile Phe Leu Glu
    290                 295                 300

Glu Thr Ser Leu Val Ala Arg Pro Gly Leu Lys Met Glu Asp Ile Gln
305                 310                 315                 320

Glu Arg Met Ala Tyr Arg Leu Lys His Leu Gly Ile Lys Val Lys Ser
                325                 330                 335

Ile Glu Glu Asp Glu Arg Cys Val Ile Pro Met Gly Gly Pro Leu Pro
                340                 345                 350

Val Leu Pro Gln Arg Val Leu Gly Ile Gly Gly Thr Ala Gly Met Val
                355                 360                 365

His Pro Ser Thr Gly Tyr Met Val Ala Arg Thr Leu Ala Ala Ala Pro
    370                 375                 380

Ile Val Ala Lys Ser Ile Ile Arg Tyr Leu Asn Asn Glu Lys Ser Met
385                 390                 395                 400

Val Ala Asp Val Thr Gly Asp Asp Leu Ala Ala Gly Ile Trp Arg Glu
                405                 410                 415

Leu Trp Pro Ile Glu Arg Arg Gln Arg Glu Phe Phe Cys Phe Gly
                420                 425                 430

Met Asp Ile Leu Leu Lys Leu Asp Leu Glu Gly Thr Arg Arg Phe Phe
        435                 440                 445

Asp Ala Phe Phe Asp Leu Glu Pro Arg Tyr Trp His Gly Phe Leu Ser
450                 455                 460
```

-continued

```
Ser Arg Leu Phe Leu Pro Glu Leu Val Thr Phe Gly Leu Ser Leu Phe
465                 470                 475                 480

Gly His Arg Ser Asn Thr Cys Arg Val Glu Ile Met Ala Lys Gly Thr
                485                 490                 495

Leu Pro Leu Ala Thr Met Ile Gly Asn Leu Val Arg Asp Arg Glu
            500                 505                 510

<210> SEQ ID NO: 3
<211> LENGTH: 991
<212> TYPE: DNA
<213> ORGANISM: Tagetes erecta
<220> FEATURE:
<221> NAME/KEY: CDS
<222> LOCATION: (51)..(923)
<223> OTHER INFORMATION: beta-hydroxylase

<400> SEQUENCE: 3
ggcacgagat tgctgtccct tgtagctcaa gaccatttgg cttaggtcga atg cgg        56
                                                        Met Arg
                                                        1 tta ctt ggt cat aaa ccc aca acc ata act tgt cac ttc ccc ttt tct     104
Leu Leu Gly His Lys Pro Thr Thr Ile Thr Cys His Phe Pro Phe Ser
        5                   10                  15 ttt tct atc aaa tca ttt acc cca att gtt agg ggc aga aga tgt act     152
Phe Ser Ile Lys Ser Phe Thr Pro Ile Val Arg Gly Arg Arg Cys Thr
    20                  25                  30 gtt tgt ttt gtt gcc ggt ggc gac agt aat agt aac agt aat aat aat     200
Val Cys Phe Val Ala Gly Gly Asp Ser Asn Ser Asn Ser Asn Asn Asn
35                  40                  45                  50 agt gac agt aat agt aat aat ccg ggt ctg gat tta aac ccg gcg gtt     248
Ser Asp Ser Asn Ser Asn Asn Pro Gly Leu Asp Leu Asn Pro Ala Val
                55                  60                  65 atg aac cgt aac cgt ttg gtt gaa gaa aaa atg gag agg aaa aaa tcg     296
Met Asn Arg Asn Arg Leu Val Glu Glu Lys Met Glu Arg Lys Lys Ser
            70                  75                  80 gaa cga ttt act tat ctt gtt gca gct att atg tct act ttt gga att     344
Glu Arg Phe Thr Tyr Leu Val Ala Ala Ile Met Ser Thr Phe Gly Ile
        85                  90                  95 act tca atg gcg gtt atg gcg gtt tat tac cgg ttt tca tgg caa atg     392
Thr Ser Met Ala Val Met Ala Val Tyr Tyr Arg Phe Ser Trp Gln Met
    100                 105                 110 gag ggt gga gaa att cct tat gtg gag atg ttt ggt aca ttt gct ctc     440
Glu Gly Gly Glu Ile Pro Tyr Val Glu Met Phe Gly Thr Phe Ala Leu
115                 120                 125                 130 tcc gtt ggt gct gcg gta gga atg gag tat tgg gca aga tgg gct cat     488
Ser Val Gly Ala Ala Val Gly Met Glu Tyr Trp Ala Arg Trp Ala His
                135                 140                 145 gag gca cta tgg cat gct tct ttg tgg cac atg cat gag tca cac cat     536
Glu Ala Leu Trp His Ala Ser Leu Trp His Met His Glu Ser His His
            150                 155                 160 aag cca cga gaa ggt ccg ttt gag ctt aat gat gtg ttt gct ata aca     584
Lys Pro Arg Glu Gly Pro Phe Glu Leu Asn Asp Val Phe Ala Ile Thr
        165                 170                 175 aat gcg gtc ccg gcc att gcg ttg ctt agt tat ggg ttt ttc cac aaa     632
Asn Ala Val Pro Ala Ile Ala Leu Leu Ser Tyr Gly Phe Phe His Lys
    180                 185                 190 ggc ata att ccg ggt ctt tgt ttt ggg gcg gga ctg gga att acg gtg     680
Gly Ile Ile Pro Gly Leu Cys Phe Gly Ala Gly Leu Gly Ile Thr Val
195                 200                 205                 210 ttt gga atg gcg tat atg ttc gtc cac gac ggg cta gtt cac aga aga     728
Phe Gly Met Ala Tyr Met Phe Val His Asp Gly Leu Val His Arg Arg
```

|   |   |   |   |   |   |   |   | 215 |   |   |   |   | 220 |   |   |   |   | 225 |   |   |   |   |
|---|---|---|---|---|---|---|---|---|---|---|---|---|---|---|---|---|---|---|---|---|---|---|
| ttc | caa | gtg | ggt | ccg | att | gcg | aat | gtt | ccc | tat | ctt | cga | agg | gtt | gca |   |   |   |   |   |   | 776 |
| Phe | Gln | Val | Gly | Pro | Ile | Ala | Asn | Val | Pro | Tyr | Leu | Arg | Arg | Val | Ala |   |   |   |   |   |   |   |
|   |   |   | 230 |   |   |   |   | 235 |   |   |   |   | 240 |   |   |   |   |   |   |   |   |   |
| gcg | gct | cat | cag | ctg | cat | cac | acg | gaa | aaa | ttt | aat | ggt | gtt | cct | tat |   |   |   |   |   |   | 824 |
| Ala | Ala | His | Gln | Leu | His | His | Thr | Glu | Lys | Phe | Asn | Gly | Val | Pro | Tyr |   |   |   |   |   |   |   |
|   |   |   | 245 |   |   |   |   | 250 |   |   |   |   | 255 |   |   |   |   |   |   |   |   |   |
| ggc | ttg | ttc | ttg | gga | cct | aag | gag | cta | gaa | gaa | gtg | ggt | ggt | acg | gaa |   |   |   |   |   |   | 872 |
| Gly | Leu | Phe | Leu | Gly | Pro | Lys | Glu | Leu | Glu | Glu | Val | Gly | Gly | Thr | Glu |   |   |   |   |   |   |   |
|   |   |   | 260 |   |   |   |   | 265 |   |   |   |   | 270 |   |   |   |   |   |   |   |   |   |
| gaa | ttg | gac | aag | gag | att | caa | aga | aga | att | aaa | ttg | tat | aat | aat | act |   |   |   |   |   |   | 920 |
| Glu | Leu | Asp | Lys | Glu | Ile | Gln | Arg | Arg | Ile | Lys | Leu | Tyr | Asn | Asn | Thr |   |   |   |   |   |   |   |
| 275 |   |   |   |   | 280 |   |   |   |   | 285 |   |   |   |   | 290 |   |   |   |   |   |   |   | aaa taaataaatt ttgtataaaa ttaatataat ttaatgatat cttttgtttt 973
Lys taaaaaaaaa aaaaaaaa 991

<210> SEQ ID NO: 4
<211> LENGTH: 291
<212> TYPE: PRT
<213> ORGANISM: Tagetes erecta

<400> SEQUENCE: 4

Met Arg Leu Leu Gly His Lys Pro Thr Thr Ile Thr Cys His Phe Pro
 1               5                  10                  15

Phe Ser Phe Ser Ile Lys Ser Phe Thr Pro Ile Val Arg Gly Arg Arg
                20                  25                  30

Cys Thr Val Cys Phe Val Ala Gly Gly Asp Ser Asn Ser Asn Ser Asn
            35                  40                  45

Asn Asn Ser Asp Ser Asn Ser Asn Asn Pro Gly Leu Asp Leu Asn Pro
        50                  55                  60

Ala Val Met Asn Arg Asn Arg Leu Val Glu Glu Lys Met Glu Arg Lys
65                  70                  75                  80

Lys Ser Glu Arg Phe Thr Tyr Leu Val Ala Ala Ile Met Ser Thr Phe
                85                  90                  95

Gly Ile Thr Ser Met Ala Val Met Ala Val Tyr Tyr Arg Phe Ser Trp
            100                 105                 110

Gln Met Glu Gly Gly Glu Ile Pro Tyr Val Glu Met Phe Gly Thr Phe
        115                 120                 125

Ala Leu Ser Val Gly Ala Ala Val Gly Met Glu Tyr Trp Ala Arg Trp
    130                 135                 140

Ala His Glu Ala Leu Trp His Ala Ser Leu Trp His Met His Glu Ser
145                 150                 155                 160

His His Lys Pro Arg Glu Gly Pro Phe Glu Leu Asn Asp Val Phe Ala
                165                 170                 175

Ile Thr Asn Ala Val Pro Ala Ile Ala Leu Leu Ser Tyr Gly Phe Phe
            180                 185                 190

His Lys Gly Ile Ile Pro Gly Leu Cys Phe Gly Ala Gly Leu Gly Ile
        195                 200                 205

Thr Val Phe Gly Met Ala Tyr Met Phe Val His Asp Gly Leu Val His
    210                 215                 220

Arg Arg Phe Gln Val Gly Pro Ile Ala Asn Val Pro Tyr Leu Arg Arg
225                 230                 235                 240

Val Ala Ala Ala His Gln Leu His Thr Glu Lys Phe Asn Gly Val
                245                 250                 255

```
Pro Tyr Gly Leu Phe Leu Gly Pro Lys Glu Leu Glu Glu Val Gly Gly
            260                 265                 270

Thr Glu Glu Leu Asp Lys Glu Ile Gln Arg Arg Ile Lys Leu Tyr Asn
        275                 280                 285

Asn Thr Lys
        290

<210> SEQ ID NO: 5
<211> LENGTH: 1887
<212> TYPE: DNA
<213> ORGANISM: Tagetes erecta
<220> FEATURE:
<221> NAME/KEY: CDS
<222> LOCATION: (141)..(1688)
<223> OTHER INFORMATION: epsilon-cyclase

<400> SEQUENCE: 5
ggcacgaggc aaagcaaagg ttgtttgttg ttgttgttga gagacactcc aatccaaaca      60
gatacaaggc gtgactggat atttctctct cgttcctaac aacagcaacg aagaagaaaa     120
agaatcatta ctaacaatca atg agt atg aga gct gga cac atg acg gca aca     173
                         Met Ser Met Arg Ala Gly His Met Thr Ala Thr
                           1               5                      10 atg gcg gct ttt aca tgc cct agg ttt atg act agc atc aga tac acg       221
Met Ala Ala Phe Thr Cys Pro Arg Phe Met Thr Ser Ile Arg Tyr Thr
            15                  20                  25 aag caa att aag tgc aac gct gct aaa agc cag cta gtc gtt aaa caa       269
Lys Gln Ile Lys Cys Asn Ala Ala Lys Ser Gln Leu Val Val Lys Gln
         30                  35                  40 gag att gag gag gaa gaa gat tat gtg aaa gcc ggt gga tcg gag ctg       317
Glu Ile Glu Glu Glu Glu Asp Tyr Val Lys Ala Gly Gly Ser Glu Leu
     45                  50                  55 ctt ttt gtt caa atg caa cag aat aag tcc atg gat gca cag tct agc       365
Leu Phe Val Gln Met Gln Gln Asn Lys Ser Met Asp Ala Gln Ser Ser
 60                  65                  70                  75 cta tcc caa aag ctc cca agg gta cca ata gga gga gga gga gac agt       413
Leu Ser Gln Lys Leu Pro Arg Val Pro Ile Gly Gly Gly Gly Asp Ser
                 80                  85                  90 aac tgt ata ctg gat ttg gtt gta att ggt tgt ggt cct gct ggc ctt       461
Asn Cys Ile Leu Asp Leu Val Val Ile Gly Cys Gly Pro Ala Gly Leu
             95                 100                 105 gct ctt gct gga gaa tca gcc aag cta ggc ttg aat gtc gca ctt atc       509
Ala Leu Ala Gly Glu Ser Ala Lys Leu Gly Leu Asn Val Ala Leu Ile
        110                 115                 120 ggc cct gat ctt cct ttt aca aat aac tat ggt gtt tgg gag gat gaa       557
Gly Pro Asp Leu Pro Phe Thr Asn Asn Tyr Gly Val Trp Glu Asp Glu
    125                 130                 135 ttt ata ggt ctt gga ctt gag ggc tgt att gaa cat gtt tgg cga gat       605
Phe Ile Gly Leu Gly Leu Glu Gly Cys Ile Glu His Val Trp Arg Asp
140                 145                 150                 155 act gta gta tat ctt gat gac aac gat ccc att ctc ata ggt cgt gcc       653
Thr Val Val Tyr Leu Asp Asp Asn Asp Pro Ile Leu Ile Gly Arg Ala
                160                 165                 170 tat gga cga gtt agt cgt gat tta ctt cac gag gag ttg ttg act agg       701
Tyr Gly Arg Val Ser Arg Asp Leu Leu His Glu Glu Leu Leu Thr Arg
            175                 180                 185 tgc atg gag tca ggc gtt tca tat ctg agc tcc aaa gtg gaa cgg att       749
Cys Met Glu Ser Gly Val Ser Tyr Leu Ser Ser Lys Val Glu Arg Ile
        190                 195                 200 act gaa gct cca aat ggc cta agt ctc ata gag tgt gaa ggc aat atc       797
Thr Glu Ala Pro Asn Gly Leu Ser Leu Ile Glu Cys Glu Gly Asn Ile
    205                 210                 215
```

```
        205                 210                 215
aca att cca tgc agg ctt gct act gtc gct tct gga gca gct tct gga      845
Thr Ile Pro Cys Arg Leu Ala Thr Val Ala Ser Gly Ala Ala Ser Gly
220                 225                 230                 235 aaa ctt ttg cag tat gaa ctt ggc ggt ccc cgt gtt tgc gtt caa aca      893
Lys Leu Leu Gln Tyr Glu Leu Gly Gly Pro Arg Val Cys Val Gln Thr
                240                 245                 250 gct tat ggt ata gag gtt gag gtt gaa agc ata ccc tat gat cca agc      941
Ala Tyr Gly Ile Glu Val Glu Val Glu Ser Ile Pro Tyr Asp Pro Ser
            255                 260                 265 cta atg gtt ttc atg gat tat aga gac tac acc aaa cat aaa tct caa      989
Leu Met Val Phe Met Asp Tyr Arg Asp Tyr Thr Lys His Lys Ser Gln
        270                 275                 280 tca cta gaa gca caa tat cca aca ttt ttg tat gtc atg cca atg tct     1037
Ser Leu Glu Ala Gln Tyr Pro Thr Phe Leu Tyr Val Met Pro Met Ser
    285                 290                 295 cca act aaa gta ttc ttt gag gaa act tgt ttg gct tca aaa gag gcc     1085
Pro Thr Lys Val Phe Phe Glu Glu Thr Cys Leu Ala Ser Lys Glu Ala
300                 305                 310                 315 atg cct ttt gag tta ttg aag aca aaa ctc atg tca aga tta aag act     1133
Met Pro Phe Glu Leu Leu Lys Thr Lys Leu Met Ser Arg Leu Lys Thr
                320                 325                 330 atg ggg atc cga ata acc aaa act tat gaa gag gaa tgg tca tat att     1181
Met Gly Ile Arg Ile Thr Lys Thr Tyr Glu Glu Glu Trp Ser Tyr Ile
            335                 340                 345 cca gta ggt gga tcc tta cca aat acc gag caa aag aac ctt gca ttt     1229
Pro Val Gly Gly Ser Leu Pro Asn Thr Glu Gln Lys Asn Leu Ala Phe
        350                 355                 360 ggt gct gct gct agc atg gtg cat cca gcc aca gga tat tcg gtt gta     1277
Gly Ala Ala Ala Ser Met Val His Pro Ala Thr Gly Tyr Ser Val Val
    365                 370                 375 aga tca ctg tca gaa gct cct aat tat gca gca gta att gca aag att     1325
Arg Ser Leu Ser Glu Ala Pro Asn Tyr Ala Ala Val Ile Ala Lys Ile
380                 385                 390                 395 tta ggg aaa gga aat tca aaa cag atg ctt gat cat gga aga tac aca     1373
Leu Gly Lys Gly Asn Ser Lys Gln Met Leu Asp His Gly Arg Tyr Thr
                400                 405                 410 acc aac atc tca aag caa gct tgg gaa aca ctt tgg ccc ctt gaa agg     1421
Thr Asn Ile Ser Lys Gln Ala Trp Glu Thr Leu Trp Pro Leu Glu Arg
            415                 420                 425 aaa aga cag aga gca ttc ttt ctc ttt gga tta gca ctg att gtc cag     1469
Lys Arg Gln Arg Ala Phe Phe Leu Phe Gly Leu Ala Leu Ile Val Gln
        430                 435                 440 atg gat att gag ggg acc cgc aca ttc ttc cgg act ttc ttc cgc ttg     1517
Met Asp Ile Glu Gly Thr Arg Thr Phe Phe Arg Thr Phe Phe Arg Leu
    445                 450                 455 ccc aca tgg atg tgg tgg ggg ttt ctt gga tct tcg tta tca tca act     1565
Pro Thr Trp Met Trp Trp Gly Phe Leu Gly Ser Ser Leu Ser Ser Thr
460                 465                 470                 475 gac ttg ata ata ttt gcg ttt tac atg ttt atc ata gca ccg cat agc     1613
Asp Leu Ile Ile Phe Ala Phe Tyr Met Phe Ile Ile Ala Pro His Ser
                480                 485                 490 ctg aga atg ggt ctg gtt aga cat ttg ctt tct gac ccg aca gga gga     1661
Leu Arg Met Gly Leu Val Arg His Leu Leu Ser Asp Pro Thr Gly Gly
            495                 500                 505 aca atg tta aaa gcg tat ctc acg ata taaataactc tagtcgcgat          1708
Thr Met Leu Lys Ala Tyr Leu Thr Ile
        510                 515 cagtttagat tataggcaca tcttgcatat atatatgtat aaaccttatg tgtgctgtat  1768
```

-continued

```
ccttacatca acacagtcat taattgtatt tcttggggta atgctgatga agtattttca    1828
ggaaaaaaaa aaaaaaaaaa ctcgagacta gttcactctc tctctcctcg tgccgattc     1887
```

<210> SEQ ID NO: 6
<211> LENGTH: 516
<212> TYPE: PRT
<213> ORGANISM: Tagetes erecta

<400> SEQUENCE: 6

```
Met Ser Met Arg Ala Gly His Met Thr Ala Thr Met Ala Ala Phe Thr
 1               5                  10                  15

Cys Pro Arg Phe Met Thr Ser Ile Arg Tyr Thr Lys Gln Ile Lys Cys
                20                  25                  30

Asn Ala Ala Lys Ser Gln Leu Val Val Lys Gln Glu Ile Glu Glu Glu
             35                  40                  45

Glu Asp Tyr Val Lys Ala Gly Gly Ser Glu Leu Leu Phe Val Gln Met
         50                  55                  60

Gln Gln Asn Lys Ser Met Asp Ala Gln Ser Ser Leu Ser Gln Lys Leu
 65                  70                  75                  80

Pro Arg Val Pro Ile Gly Gly Gly Asp Ser Asn Cys Ile Leu Asp
                 85                  90                  95

Leu Val Val Ile Gly Cys Gly Pro Ala Gly Leu Ala Leu Ala Gly Glu
                100                 105                 110

Ser Ala Lys Leu Gly Leu Asn Val Ala Leu Ile Gly Pro Asp Leu Pro
             115                 120                 125

Phe Thr Asn Asn Tyr Gly Val Trp Glu Asp Glu Phe Ile Gly Leu Gly
         130                 135                 140

Leu Glu Gly Cys Ile Glu His Val Trp Arg Asp Thr Val Val Tyr Leu
145                 150                 155                 160

Asp Asp Asn Asp Pro Ile Leu Ile Gly Arg Ala Tyr Gly Arg Val Ser
                165                 170                 175

Arg Asp Leu Leu His Glu Glu Leu Leu Thr Arg Cys Met Glu Ser Gly
             180                 185                 190

Val Ser Tyr Leu Ser Ser Lys Val Glu Arg Ile Thr Glu Ala Pro Asn
         195                 200                 205

Gly Leu Ser Leu Ile Glu Cys Glu Gly Asn Ile Thr Ile Pro Cys Arg
     210                 215                 220

Leu Ala Thr Val Ala Ser Gly Ala Ala Ser Gly Lys Leu Leu Gln Tyr
225                 230                 235                 240

Glu Leu Gly Gly Pro Arg Val Cys Val Gln Thr Ala Tyr Gly Ile Glu
                245                 250                 255

Val Glu Val Glu Ser Ile Pro Tyr Asp Pro Ser Leu Met Val Phe Met
             260                 265                 270

Asp Tyr Arg Asp Tyr Thr Lys His Lys Ser Gln Ser Leu Glu Ala Gln
         275                 280                 285

Tyr Pro Thr Phe Leu Tyr Val Met Pro Met Ser Pro Thr Lys Val Phe
     290                 295                 300

Phe Glu Glu Thr Cys Leu Ala Ser Lys Glu Ala Met Pro Phe Glu Leu
305                 310                 315                 320

Leu Lys Thr Lys Leu Met Ser Arg Leu Lys Thr Met Gly Ile Arg Ile
                325                 330                 335

Thr Lys Thr Tyr Glu Glu Glu Trp Ser Tyr Ile Pro Val Gly Gly Ser
             340                 345                 350
```

-continued

```
Leu Pro Asn Thr Glu Gln Lys Asn Leu Ala Phe Gly Ala Ala Ala Ser
            355                 360                 365

Met Val His Pro Ala Thr Gly Tyr Ser Val Val Arg Ser Leu Ser Glu
    370                 375                 380

Ala Pro Asn Tyr Ala Ala Val Ile Ala Lys Ile Leu Gly Lys Gly Asn
385                 390                 395                 400

Ser Lys Gln Met Leu Asp His Gly Arg Tyr Thr Thr Asn Ile Ser Lys
                405                 410                 415

Gln Ala Trp Glu Thr Leu Trp Pro Leu Glu Arg Lys Arg Gln Arg Ala
            420                 425                 430

Phe Phe Leu Phe Gly Leu Ala Leu Ile Val Gln Met Asp Ile Glu Gly
                435                 440                 445

Thr Arg Thr Phe Arg Thr Phe Phe Arg Leu Pro Thr Trp Met Trp
    450                 455                 460

Trp Gly Phe Leu Gly Ser Ser Leu Ser Ser Thr Asp Leu Ile Ile Phe
465                 470                 475                 480

Ala Phe Tyr Met Phe Ile Ile Ala Pro His Ser Leu Arg Met Gly Leu
                485                 490                 495

Val Arg His Leu Leu Ser Asp Pro Thr Gly Gly Thr Met Leu Lys Ala
                500                 505                 510

Tyr Leu Thr Ile
        515

<210> SEQ ID NO: 7
<211> LENGTH: 1020
<212> TYPE: DNA
<213> ORGANISM: Tagetes erecta
<220> FEATURE:
<221> NAME/KEY: CDS
<222> LOCATION: (101)..(796)
<223> OTHER INFORMATION: IPP isomerase

<400> SEQUENCE: 7
caggaattcg gcacgagctc aatctcaatc aaccctcttc ttctctccca gtatctatac      60
caaaaacaac tcaaatctcc tccgtcgctc ttactccgcc atg ggt gac gac tcc     115
                                              Met Gly Asp Asp Ser
                                                1               5 ggc atg gat gct gtt cag cga cgt ctc atg ttt aac gat gaa tgc att     163
Gly Met Asp Ala Val Gln Arg Arg Leu Met Phe Asn Asp Glu Cys Ile
            10                  15                  20 ttg gtg gat gag tgt gac aat gtg gtg gga cat gat acc aaa tac aat     211
Leu Val Asp Glu Cys Asp Asn Val Val Gly His Asp Thr Lys Tyr Asn
        25                  30                  35 tgt cac ttg atg gag aag att gaa aca ggt aaa atg ctg cac aga gca     259
Cys His Leu Met Glu Lys Ile Glu Thr Gly Lys Met Leu His Arg Ala
    40                  45                  50 ttc agc gtt ttt cta ttc aat tca aaa tac gag tta ctt ctt cag caa     307
Phe Ser Val Phe Leu Phe Asn Ser Lys Tyr Glu Leu Leu Leu Gln Gln
55                  60                  65 cgg tct gca acc aag gtg aca ttt cct tta gta tgg acc aac acc tgt     355
Arg Ser Ala Thr Lys Val Thr Phe Pro Leu Val Trp Thr Asn Thr Cys
        70                  75                  80                  85 tgc agc cat cca ctc tac aga gaa tcc gag ctt gtt ccc gaa aac gcc     403
Cys Ser His Pro Leu Tyr Arg Glu Ser Glu Leu Val Pro Glu Asn Ala
                90                  95                  100 ctt gga gta aga aat gct gca cag agg aag ctg ttg gat gaa ctc ggt     451
Leu Gly Val Arg Asn Ala Ala Gln Arg Lys Leu Leu Asp Glu Leu Gly
            105                 110                 115
```

```
atc cct gct gaa gat gtt ccc gtt gat cag ttt act cct tta ggt cgc    499
Ile Pro Ala Glu Asp Val Pro Val Asp Gln Phe Thr Pro Leu Gly Arg
        120                 125                 130 atg ctc tac aag gct cca tct gat gga aag tgg gga gaa cat gaa ctt    547
Met Leu Tyr Lys Ala Pro Ser Asp Gly Lys Trp Gly Glu His Glu Leu
135                 140                 145 gac tac cta ctt ttc ata gtg aga gac gtt gct gta aac ccg aac cca    595
Asp Tyr Leu Leu Phe Ile Val Arg Asp Val Ala Val Asn Pro Asn Pro
150                 155                 160                 165 gat gaa gtg gcg gat atc aaa tat gtg aac caa gaa gag tta aag gag    643
Asp Glu Val Ala Asp Ile Lys Tyr Val Asn Gln Glu Glu Leu Lys Glu
                170                 175                 180 ctg cta agg aaa gca gat gcg ggg gag gag ggt ttg aag ctg tct cca    691
Leu Leu Arg Lys Ala Asp Ala Gly Glu Glu Gly Leu Lys Leu Ser Pro
            185                 190                 195 tgg ttc agg tta gtg gtt gat aac ttc ttg ttc aag tgg tgg gat cat    739
Trp Phe Arg Leu Val Val Asp Asn Phe Leu Phe Lys Trp Trp Asp His
        200                 205                 210 gtg caa aag gtt aca ctc act gaa gca att gat atg aaa acc ata cac    787
Val Gln Lys Val Thr Leu Thr Glu Ala Ile Asp Met Lys Thr Ile His
    215                 220                 225 aag ctg ata tagaaacaca ccctcaaccg aaaagttcaa gcctaataat           836
Lys Leu Ile
230 tcgggttggg tcgggtctac catcaattgt tttttctttt taagaagttt taatctctat  896 ttgagcatgt tgattcttgt cttttgtgtg taagattttg ggtttcgttt cagttgtaat  956 aatgaaccat tgatggtttg caatttcaag ttcctatcga caaaaaaaa aaaaaaaaa   1016 actc                                                              1020

<210> SEQ ID NO: 8
<211> LENGTH: 232
<212> TYPE: PRT
<213> ORGANISM: Tagetes erecta

<400> SEQUENCE: 8

Met Gly Asp Asp Ser Gly Met Asp Ala Val Gln Arg Arg Leu Met Phe
1               5                   10                  15

Asn Asp Glu Cys Ile Leu Val Asp Glu Cys Asp Asn Val Val Gly His
            20                  25                  30

Asp Thr Lys Tyr Asn Cys His Leu Met Glu Lys Ile Glu Thr Gly Lys
        35                  40                  45

Met Leu His Arg Ala Phe Ser Val Phe Leu Phe Asn Ser Lys Tyr Glu
    50                  55                  60

Leu Leu Leu Gln Gln Arg Ser Ala Thr Lys Val Thr Phe Pro Leu Val
65                  70                  75                  80

Trp Thr Asn Thr Cys Cys Ser His Pro Leu Tyr Arg Glu Ser Glu Leu
                85                  90                  95

Val Pro Glu Asn Ala Leu Gly Val Arg Asn Ala Ala Gln Arg Lys Leu
            100                 105                 110

Leu Asp Glu Leu Gly Ile Pro Ala Glu Asp Val Pro Val Asp Gln Phe
        115                 120                 125

Thr Pro Leu Gly Arg Met Leu Tyr Lys Ala Pro Ser Asp Gly Lys Trp
    130                 135                 140

Gly Glu His Glu Leu Asp Tyr Leu Leu Phe Ile Val Arg Asp Val Ala
145                 150                 155                 160

Val Asn Pro Asn Pro Asp Glu Val Ala Asp Ile Lys Tyr Val Asn Gln
```

```
                        165                 170                   175
Glu Glu Leu Lys Glu Leu Leu Arg Lys Ala Asp Ala Gly Glu Glu Gly
                180                 185                 190

Leu Lys Leu Ser Pro Trp Phe Arg Leu Val Val Asp Asn Phe Leu Phe
                195                 200                 205

Lys Trp Trp Asp His Val Gln Lys Val Thr Leu Thr Glu Ala Ile Asp
    210                 215                 220

Met Lys Thr Ile His Lys Leu Ile
225                 230
```

MARIGOLD DNA ENCODING BETA-CYCLASE

BACKGROUND OF THE INVENTION (1) Field of the Invention

The present invention provides a method for manipulating the ratio of various carotenoids in plants as a means for augmenting the accumulation of selected carotenoids. The present invention further relates to transgenic marigold plants which produce various ratios of carotenoids and methods for producing the same. Preferably, various carotenoids can be accumulated in the petals of marigold by selecting a specific combination of isolated DNAs encoding various enzymes involved in the carotenoid biosynthesis pathway to produce antisense RNA, sense RNA or combinations thereof. The present invention also describes isolated DNA sequences encoding the marigold genes beta-cyclase, epsilon-cyclase, beta-hydroxylase, isopentyl pyrophosphate isomerase.

(2) Description of the Related Art

Carotenoids which comprise the most important group of 40-carbon terpenes and terpenoids are pigments that have a variety of commercial applications. Carotenoids are a class of hydrocarbons (carotenes) and their hydroxylated derivatives (xanthophylls) which comprise 40-carbon ($C_{40}$) terpenoids consisting of eight isoprenoid ($C_5$) units joined together. The terpenoids are joined in such a manner that the arrangement of the isoprenoid units is reversed at the center of the molecule placing the terminal methyl groups in a 1,6 relationship and the non-terminal methyl groups in a 1,5 relationship. Carotenoids can be monocyclic, bicyclic or acyclic. Carotenoids are produced by a wide variety of bacteria, fungi, and green plants. The carotenoids of the most value are intermediates in the carotenoid biosynthetic pathway and consist of lycopene ($\psi,\psi$-carotene), beta-carotene ($\beta,\beta$-carotene), zeaxanthin ($\beta,\beta$-carotene-3,3'-diol), astaxanthin ($\beta,\beta$-carotene-3,3'-diol-4,4'-diketo), lutein ($\beta,\epsilon$-carotene-3,3'-diol) and alpha-carotene ($\beta,\epsilon$-carotene).

Lycopene is a red carotenoid and has utility as a food colorant. Lycopene is naturally synthesized from the precursor phytoene through a series of four separate dehydrogenation steps by the removal of eight atoms of hydrogen. Lycopene is an intermediate in the biosynthesis of other carotenoids in some bacteria, fungi, and all green plants.

Beta-carotene is an orange carotenoid that is naturally produced from lycopene through the intermediate gamma-carotene $\beta,\psi$-carotene) by two sequential cyclization reactions that produce beta rings at the termini. Beta-carotene is useful as a colorant for margarine, butter and cheese, and as a provitamin which has been suggested to have a role in cancer prevention. Current commercial methods for producing beta-carotene include isolation from carrots, chemical synthesis and microbial production.

Zeaxanthin is a yellow carotenoid that is naturally produced from beta-carotene through the intermediate beta-cryptoxanthin by hydrogenation reactions which add hydroxyl groups to the beta rings at both termini. Zeaxanthin is used as a colorant in the poultry industry. Zeaxanthin can be synthesized chemically, however current chemical synthesis reactions are inefficient and are not commercially competitive. Therefore, zeaxanthin is usually produced by extraction from corn grain and corn gluten meal. However, all of these plant sources are characterized by low and inconsistent production levels.

Alpha-carotene is another yellow carotenoid that is naturally produced from lycopene through the intermediate δ-carotene ($\epsilon,\psi$-carotene) by two sequential cyclization reactions at the termini that produces one terminus with an epsilon ring and the other terminus with a beta ring. Alpha-carotene is useful as a colorant and as a provitamin.

Carotenoids have a variety of commercial uses ranging from use as a pigment to color foods and cosmetics to uses by the pharmacological industry. Pharmacological uses include use as a control during manufacture to distinguish one drug product from another, as an active component of various medicinal compositions, and as a vitamin supplement for humans. Carotenoids are also used as a dietary supplement in animal and poultry feedstuffs. Carotenoids haven even been used as a photoconductor in recording-media film.

In humans and animals carotenoids have diverse biological functions, and despite the similarity in structure, have different roles. Certain carotenoids are precursors to vitamin A which can be converted to vitamin A by the body, examples are beta-carotene, alpha-carotene, and alpha-cryptoxanthin.

Aside from a role as a precursor to vitamin A, carotenoids are effective quenchers of oxygen free radicals, with lycopene exhibiting the highest quenching activity. Carotenoids function as chain-breaking antioxidants and therefore protect the body from damage by free radicals. Free radicals have been implemented in wide range of human ailments such as onset of pre-mature aging, cancer, atherosclerosis, cataracts, and an array of degenerative diseases. Carotenoids have also been shown to enhance the immune system and to protect the skin from UV damage.

At present only a few plants are widely used to produce carotenoids. However, production of carotenoids from plants is expensive because of the low yields and variability of production. Recombinant DNA technology is a means for increasing the productive capacity of carotenoid biosynthesis in plants.

In U.S. Pat. No. 5,429,939 to Misawa et al DNA segments from *Erwinia uredovora* encoding bacterial enzymes geranylgeranyl pyrophosphate synthase, zeaxanthin glycosylase, lycopene cyclase, lycopene synthase, phytoene synthase, and beta-carotene hydroxylase are disclosed. The abovementioned U.S. patent provides a process for producing a carotenoid or a precursor compound in a host but the invention does not provide a means for controlling the ratio of specific carotenoids in a plant.

In U.S. Pat. No. 5,530,188 to Ausich et al DNA segments encoding *Erwinia herbicola* enzymes geranylgeranyl pyrophosphate, phytoene synthase, phytoene dehydrogenase-4H, and lycopene cyclase are disclosed. The abovementioned patent provides a means for producing beta-carotene in a plant containing the DNA segment encoding lycopene cyclase. However, the U.S. patent does not provide a means for controlling the ratio of specific carotenoids in a plant thereby producing plants that produce other valuable carotenoids.

In U.S. Pat. No. 5,618,988 to Hauptmann et al, recombinant DNA technology was used to enhance carotenoid accumulation in the storage organs of genetically engineered plants by introducing into the plant a vector comprising a chimeric polypeptide consisting of the bacterial gene encoding phytoene synthase conjugated to a plastid transit peptide. The phytoene synthase was derived from the bacterium *Erwinia herbicola*. While the abovementioned U.S. patent provides a means for increasing production of phytoene which then serves as a precursor to pigmented carotenoids, the patent does not provide a means for controlling the ratio of specific carotenoids in a plant thereby producing plants that produce specific valuable carotenoids.

In U.S. Pat. No. 5,684,238 to Ausich et al DNA segments from *Erwinia herbicola* encoding enzymes geranylgeranyl pyrophosphate synthase, phytoene synthase, phytoene dehydrogenase-4H, lycopene cyclase, beta-carotene hydroxylase, and zeaxanthin glycosylase are disclosed. The abovementioned patent provides a means for producing zeaxanthin or glycosylated zeaxanthin in a culture containing a precursor and a host containing one or more said DNA segments or a transformed plant containing said beta-carotene hydroxylase. However, the U.S. patent does not provide a means for controlling the ratio of other carotenoids in a plant thereby producing plants that produce other valuable carotenoids.

In U.S. Pat. No. 5,744,341 to Cunningham, Jr. et al DNA segments from *Arabidopsis thaliana* encoding the eucaryote enzymes epsilon-cyclase and beta-hydroxylase, and DNA segments from *Arabidopsis thaliana* and bacterium *Haematococcus pluvialis* encoding the enzyme isopentyl pyrophosphate isomerase are disclosed. The U.S. patent suggests uses for the disclosed DNA segments, however the patent does not provide a means for controlling the ratio of specific carotenoids in a plant species using DNA segments encoding various carotenoid biosynthesis enzymes from the same species thereby producing plants that produce other valuable carotenoids.

In U.S. Pat. No. 5,750,865 to Bird et al DNA segments homologous to part or all of the clone pTOM from tomato is provided as a means to modify carotenoid biosynthesis in plants by promoting or inhibiting the synthesis of various carotenoids. The clone pTOM encodes an enzyme with a significant degree of homology to the crtB gene of *Rhodobacter capsulatus* which encodes phytoene synthase. The abovementioned invention is used to promote or inhibit the carotenoid biosynthetic pathway, but the invention does not provide a means for controlling the ratio of specific carotenoids in a plant.

Although the above techniques have been successful in providing enhanced levels of certain carotenoids in bacterial hosts when the appropriate carotenoid precursor is provided to the host, it would be preferable to utilize a higher plant species wherein technical maintenance procedures would be minimized and yield of specific carotenoids could be optimized. While U.S. patents to Hauptmann et al and Ausich et al disclose uses in higher plants, the carotenoid enzymes disclosed are of bacterial origin which are structurally distinct from the carotenoid enzymes of eucaryote origin. It is well known in the art that an enzyme from a bacterium can be functionally similar to an enzyme from a eucaryote, however the enzymes are rarely structurally related and in many cases the enzymes can possess different secondary functions that in the heterologous host can be undesirable. While U.S. patents to Bird et al and Cunningham et al disclose several DNA segments encoding carotenoid biosynthesis enzymes, the proposed uses for said DNA segments are in heterologous hosts which in certain cases may result in undesirable side effects.

Therefore, there still remains a need for isolation of DNA sequences encoding other carotenoid biosynthetic enzymes from other higher plants. There also remains a need to manipulate the carotenoid biosynthetic pathway in plants to enhance production of specific carotenoid compounds. Finally, there remains a need for transformed plant species, wherein each variety of transformed plant species comprises a combination of DNA sequences derived from a plant which when in the transformed plant species affects the accumulation of specific carotenoid compounds.

SUMMARY OF THE INVENTION

The present invention provides a transgenic plant material containing an isolated DNA encoding a marigold enzyme having catalytic activity of beta-cyclase. The present invention also provides a transgenic plant material containing an isolated DNA encoding a marigold enzyme having catalytic activity of beta-hydroxylase. The present invention further provides a transgenic plant material containing an isolated DNA encoding a marigold enzyme having catalytic activity of epsilon-cyclase, and further still, a transgenic plant material containing an isolated DNA encoding a marigold IPP isomerase. The present invention further provides a transgenic plant material containing more than one isolated DNA encoding a marigold enzyme having catalytic activity of an enzyme selected from the group consisting beta-cyclase, beta-hydroxylase, epsilon-cyclase and isopentyl pyrophosphate (IPP) isomerase.

The present invention provides a transgenic plant material containing an isolated DNA encoding a marigold enzyme having catalytic activity of beta-cyclase which produces an RNA antisense to an mRNA encoding beta-cyclase. The present invention also provides a transgenic plant material containing an isolated DNA encoding a marigold enzyme having catalytic activity of beta-hydroxylase which produces an RNA antisense to an mRNA encoding beta-hydroxylase. The present invention further provides a transgenic plant material containing an isolated DNA encoding a marigold enzyme having catalytic activity of epsilon-cyclase which produces an RNA antisense to an mRNA encoding epsilon-cyclase. The present invention further provides a transgenic plant material containing more than one isolated DNA encoding a marigold enzyme having catalytic activity of an enzyme selected from the group consisting beta-cyclase, beta-hydroxylase and epsilon-cyclase wherein the RNA produced by the isolated DNA is antisense to an mRNA encoding an enzyme selected from the group consisting of beta-cyclase, beta-hydroxylase and epsilon-cyclase.

The present invention further provides a transgenic plant material containing more than one isolated DNA encoding a marigold enzyme having catalytic activity of an enzyme selected from the group consisting beta-cyclase, beta-hydroxylase and epsilon-cyclase wherein the RNA produced by at least one of the isolated DNAs is antisense to an mRNA encoding an enzyme selected from the group consisting of beta-cyclase, beta-hydroxylase and epsilon-cyclase.

Thus, the present invention provides genetically engineered marigold plants that over-produce a desired carotenoid pigment in the petal. The present invention further provides a method for transforming marigold plants with various combinations of isolated DNAs which encode at least one of the enzymes selected from the group consisting of beta-cyclase, epsilon-cyclase, beta-hydroxylase, IPP isomerase and epsilon-hydroxylase. The present invention allows the use of marigolds, a plant with known agronomic traits to produce a range of carotenoids in amounts that previously were not economically produced by traditional agricultural methods.

In the present invention, an isolated DNA encoding one or more of the enzymes selected from the group consisting of beta-cyclase, epsilon-cyclase and beta-hydroxylase is operably linked to a promoter in the antisense orientation. The isolated DNA is introduced into the plant to make a transgenic plant. The isolated DNA in the plant is transcribed into an antisense RNA which is complementary to the mRNA transcribed from the corresponding carotenoid biosynthesis pathway gene in the plant's genome. The antisense RNA and the plant's mRNA form a double-stranded RNA duplex with the mRNA which inhibits translation of the mRNA, preventing synthesis of the enzyme. The isolated DNA can range in length from 50 nucleotides to the full length of the mRNA.

In another embodiment of the present invention an isolated DNA encoding one or more of the enzymes selected from the group consisting of beta-cyclase, epsilon-cyclase, beta-hydroxylase and IPP isomerase is operably linked to a promoter in the sense orientation. The isolated DNA is introduced into the plant to make a transgenic plant. The isolated DNA in the plant is transcribed into an mRNA which is additive to the mRNA that is concurrently transcribed from the corresponding carotenoid biosynthesis pathway gene in the plant's genome. Thus an excess of mRNA encoding the desired carotenoid synthesis enzyme is produced. The excess mRNA is translated into the wanted enzyme producing an excess of the enzyme. Since there is an now an excess of the this enzyme, the excess enzyme out competes with other enzymes in the pathway for substrate. Thus, the carotenoid biosynthesis pathway is shifted towards the direction of those carotenoid products produced by the wanted enzyme.

In a third embodiment, a first isolated DNA encoding one or more of the enzymes selected from the group consisting of beta-cyclase, epsilon-cyclase, beta-hydroxylase, and epsilon-hydroxylase is operably linked to a promoter in the antisense orientation and a second DNA encoding one or more enzymes from the group not selected for antisense expression or IPP isomerase is operably linked to a promoter in the sense orientation. The isolated DNA is introduced into the plant to make a transgenic plant. The first DNA in the plant is transcribed into an antisense RNA which is complementary to the mRNA transcribed from the corresponding carotenoid biosynthesis pathway gene in the plant's genome. The second isolated DNA in the plant is transcribed into an mRNA which is additive to the mRNA transcribed from the corresponding carotenoid biosynthesis pathway gene in the plant's genome causing an excess of the enzyme to be produced. The simultaneous inhibition of certain of these enzymes and overproduction of other of these enzymes causes the preferential accumulation of specific carotenoid products.

The preferred promoter to produce the anti-sense or the sense RNA is a promoter that specifically operates in the petals of the plant. Thus the carotenoid accumulates in the flower of the plant.

Transgenic plants containing the marigold genes regulated by the preferred petal-specific promoter allows the greatest level of production of the selected carotenoids in the petal of the transgenic plant to be achieved without affecting other tissues of the plant.

OBJECTS

It is an object of the present invention to provide isolated DNA sequences from marigold plants which encode enzymes involved in the carotenoid biosynthesis pathway. The isolated DNA sequences encode enzymes selected from the group consisting of beta-cyclase, epsilon-cyclase, beta-hydroxylase and IPP isomerase. It is also an object to provide a petal specific promoter to produce RNA from the isolated DNA in the petal of the plant.

Another object of the present invention is to provide a method for producing a carotenoid in a marigold plant selected from the group consisting of beta-carotene, alpha-carotene, zeaxanthin, lycopene, zeinoxanthin, beta-cryptoxanthin, and combination thereof using the above-mentioned isolated DNA sequences to produce RNA in the plant that are antisense to the mRNA concurrently produced by the plant. Therefore, a plant transformed with a vector that produces RNA antisense to epsilon-cyclase mRNA will cause the plant to preferentially accumulate zeaxanthin; a plant transformed with vectors that produce RNA antisense to epsilon-cyclase and beta-cyclase mRNAs will cause the plant to preferentially accumulate lycopene; a plant transformed with vectors that produce RNA antisense to epsilon-hydroxylase and beta-hydroxylase mRNAs will cause the plant to preferentially accumulate alpha-carotene; and a plant transformed with vectors that produce RNA antisense to epsilon-cyclase and beta-hydroxylase mRNAs will cause the plant to preferentially accumulate beta-carotene.

Another object of the present invention is to produce transgenic marigold which overproduce specific carotenoid biosynthesis enzymes which then causes the preferential accumulation of specific carotenoids in the petal. To accomplish the objective, the isolated DNA sequences are operably linked to a promoter in the sense orientation to produce a mRNA in the sense orientation. The present invention further provides for transformed marigold plants containing one or more of the isolated DNA sequences in the plant which causes an excess of each of the enzyme encoded by the isolated DNA to be made. The excess enzyme encoded by the isolated DNA affects the ratio of specific carotenoids in the transgenic plant, causing the over accumulation of specific carotenoids. The carotenoids to be overproduced are selected from the group consisting of beta-carotene, alpha-carotene, zeaxanthin, lycopene, zeinoxanthin, beta-cryptoxanthin, rubixanthin, and combination thereof.

Further still an object of the present invention is to provide transformed marigold plants containing various combinations of the isolated DNA sequences wherein certain DNA sequences are operably linked to a promoter which produce RNA in the sense orientation and other DNA sequences are operably linked to a promoter which produce RNA in the antisense orientation. The invention can be used to overproduce a carotenoid selected from the group consisting of beta-carotene, alpha-carotene, zeaxanthin, lycopene, zeinoxanthin, beta-cryptoxanthin, rubixanthin, and combination thereof.

These and other objects will become increasingly apparent by reference to the following description and the drawings.

DETAILED DESCRIPTION OF THE DRAWINGS

FIG. 3 is the DNA sequence for beta-cyclase (SEQ ID NO:1).

FIG. 4 is the amino acid sequence for beta-cyclase (SEQ ID NO:2).

FIG. 5 is the DNA sequence for epsilon-cyclase (SEQ ID NO:3).

FIG. 6 is the amino acid sequence for epsilon-cyclase (SEQ ID NO:4).

FIG. 7 is the DNA sequence for beta-hydroxylase (SEQ ID NO:5).

FIG. 8 is the amino acid sequence for beta-hydroxylase (SEQ ID NO:6).

FIG. 9 is the DNA sequence for isopentyl pyrophosphate (IPP) isomerase (SEQ ID NO:7).

FIG. 10 is the amino acid sequence for IPP isomerase (SEQ ID NO:8).

DETAILED DESCRIPTION OF THE INVENTION

Figure 1:
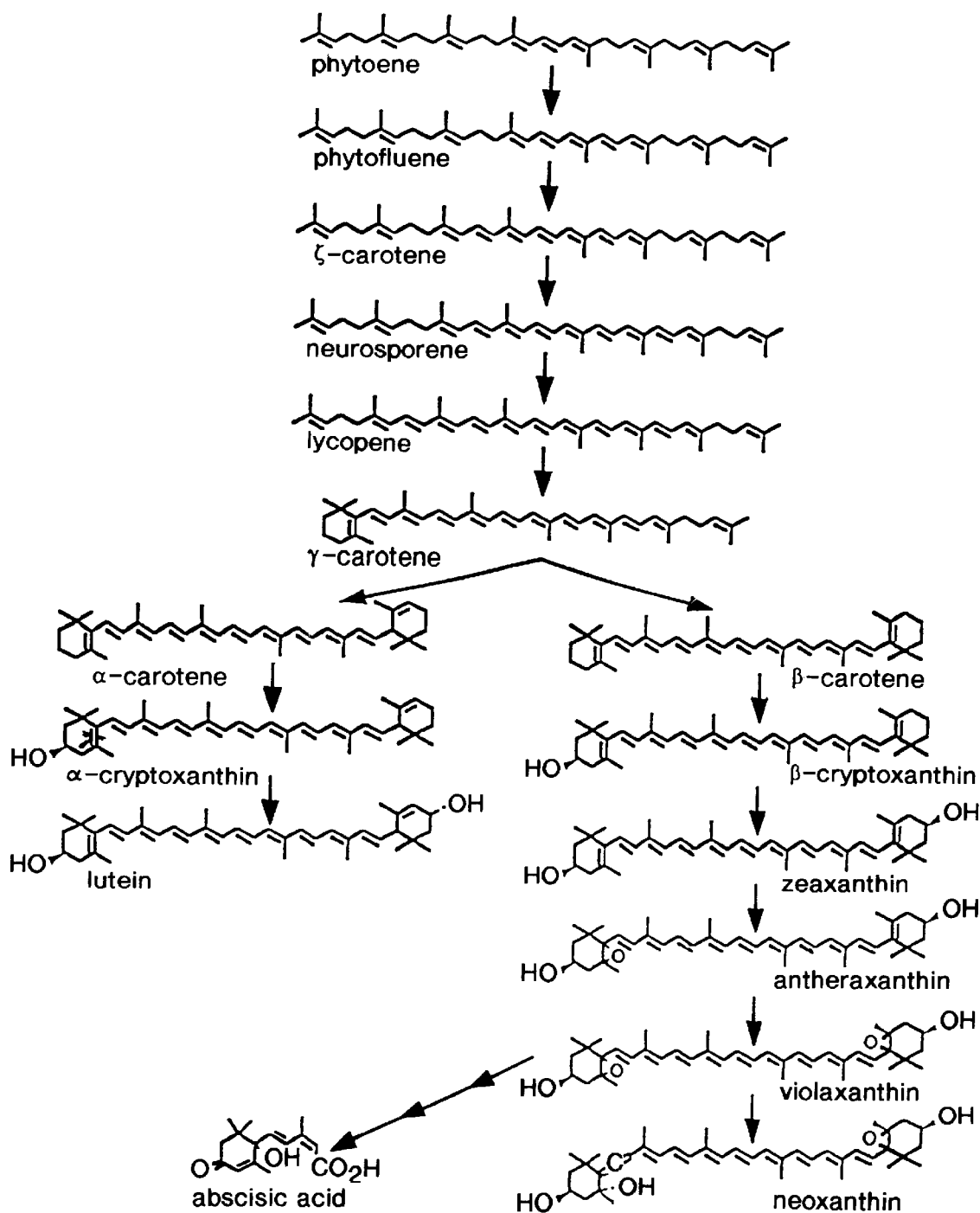
FIG. 1 is a flow diagram showing a part of the carotenoid pathway in higher plants.

To facilitate the detailed description of the present invention, it is helpful to set forth definitions of certain terms to be used hereinafter.

Amino acids are the structural units comprising a polypeptide.

Nucleic acids are the structural units comprising a DNA or RNA molecule.

Transcription means the formation of a RNA chain in accordance with the genetic information contained in the DNA. When the genetic information encodes a structural gene, the RNA so formed is referred to as mRNA.

Translation means the process whereby genetic information in an mRNA molecule directs the order of specific amino acids during protein synthesis.

Expression means the combination of cellular processes, including transcription and translation undergone by a structural gene to produce a polypeptide.

Expression vector means a plasmid or phage comprising a DNA sequence operably linked to a promoter which in a cell causes transcription of the DNA into an RNA molecule. The RNA molecule can be translated into a polypeptide.

Operably linked means a DNA sequence linked to a promoter wherein the promoter causes the DNA sequence to be transcribed into an RNA molecule. The DNA sequence can comprise a structural gene, a portion of a structural gene, or a structural gene or portion thereof in the antisense orientation.

Promoter means a DNA sequence which causes transcription of DNA into a RNA molecule. For purposes herein, promoter is used to denote DNA sequences that permit transcription in a plant.

Recombinant DNA molecule means a hybrid DNA sequence comprising at least two nucleotide sequences not normally found together in nature.

Structural gene means a DNA sequence that is transcribed into an mRNA which is then translated into a polypeptide.

Vector means a DNA molecule that is capable of replicating in a cell and to which another DNA sequence can be operably linked so as to bring about replication of the attached DNA sequence. Commonly used vectors are bacterial plasmids and bacteriophages.

Sense refers to the sequence of the DNA strand of a structural gene that is transcribed into an mRNA molecule copy which is then translated into the polypeptide encoded by the structural gene.

Antisense refers to the sequence of the DNA strand that is complementary to the sequence of the sense strand and cannot be translated into the polypeptide encoded by the structural gene. For purposes of the present invention, antisense refers to a DNA that is operably linked to a promoter in the reverse orientation such that when the DNA is transcribed, an antisense RNA molecule is produced that has a nucleotide sequence that is complementary to and capable of hybridizing to an mRNA produced from the same DNA sequence in the sense orientation.

Polypeptide means the sequence of amino acids that comprise a structural gene. The term protein is equivalent to the term polypeptide. Enzymes are polypeptides.

Transformation means the process of introducing DNA into an organism which changes the genotype of the recipient organism in a stable manner. Transformation encompasses the introduction of the DNA by whatever means.

Transgenic plant means a plant which by the process of transformation is made to contain DNA sequences which are not normally present in the plant or DNA sequences which are in addition to the sequences which are normally present in the plant.

Polyadenylation site is the nucleotide sequence which causes certain enzymes to cleave mRNA at a specific site and to add a sequence of adenylic acid residues to the 3' end of the mRNA.

Marigold flowers have been used by the food and feed industries as a source of carotenoid pigments. The object of the present invention is to genetically engineer marigold plants to over-produce in the petals a desired carotenoid pigment. Marigold petals normally contain 1 to 3% zeaxanthin and greater than 90% lutein. Marigold plants transformed with various combinations of isolated DNAs which encode at least one of the enzymes selected from the group consisting of beta-cyclase, epsilon-cyclase, beta-hydroxylase and IPP isomerase. The transformed marigold plants are genetically engineered wherein certain genes of the carotenoid biosynthesis pathway (FIG. 1) are either over-expressed or suppressed to deviate the carotenoid synthesis pathway in the desired direction which thus causes accumulation of desired carotenoids.

The carotenoids are preferably accumulated in the marigold flowers by using petal specific promoters operably linked to the abovementioned isolated DNAs. The petal-specific promoter allows the modification of carotenoid biosynthesis to be relegated to the petals of the transgenic plant. This allows carotenoid production to be manipulated without affecting or harming other tissues of the plant. Standard technology can be used to isolate the accumulated carotenoids from the flowers of the transformed marigolds. The present invention allows the use of marigolds, a plant with known agronomic traits to produce a range of carotenoids and in amounts that previously were not economically produced by traditional agricultural methods.

Carotenoids are the most widespread group of pigments found in virtually all photosynthetic organisms and certain non-photosynthetic bacteria and fungi. In photosynthetic organisms, carotenoids are an essential component of the photosynthetic pathway. Glyceraldehyde-3-phosphate and pyruvate are used as substrates to produce DMAPP by a series of reactions known as the alternative IPP pathway. Many of the enzymes involved have as yet to be described and cloned. DMAPP is converted to IPP and then geryanylgeranyl pyrophosphate (GGPP) through an isomerization reaction catalyzed by IPP isomerase followed by a series of condensation reactions by GGPP synthase. GGPP is dimerized by phytoene synthase to form phytoene, the first $C_{40}$ carotenoid.

The part of the carotenoid biosynthesis pathway in higher plants that proceeds from phytoene is shown in FIG. 1. Phytoene is converted to the first pigment carotenoid, lycopene, through a series of dehydrogenation reactions catalyzed by one or more desaturases. Lycopene can serve as a precursor for a variety of other pigmented carotenoids.

Lycopene can be converted to beta-carotene through two sequential cyclization reactions catalyzed by beta-cyclase.

Figure 2:
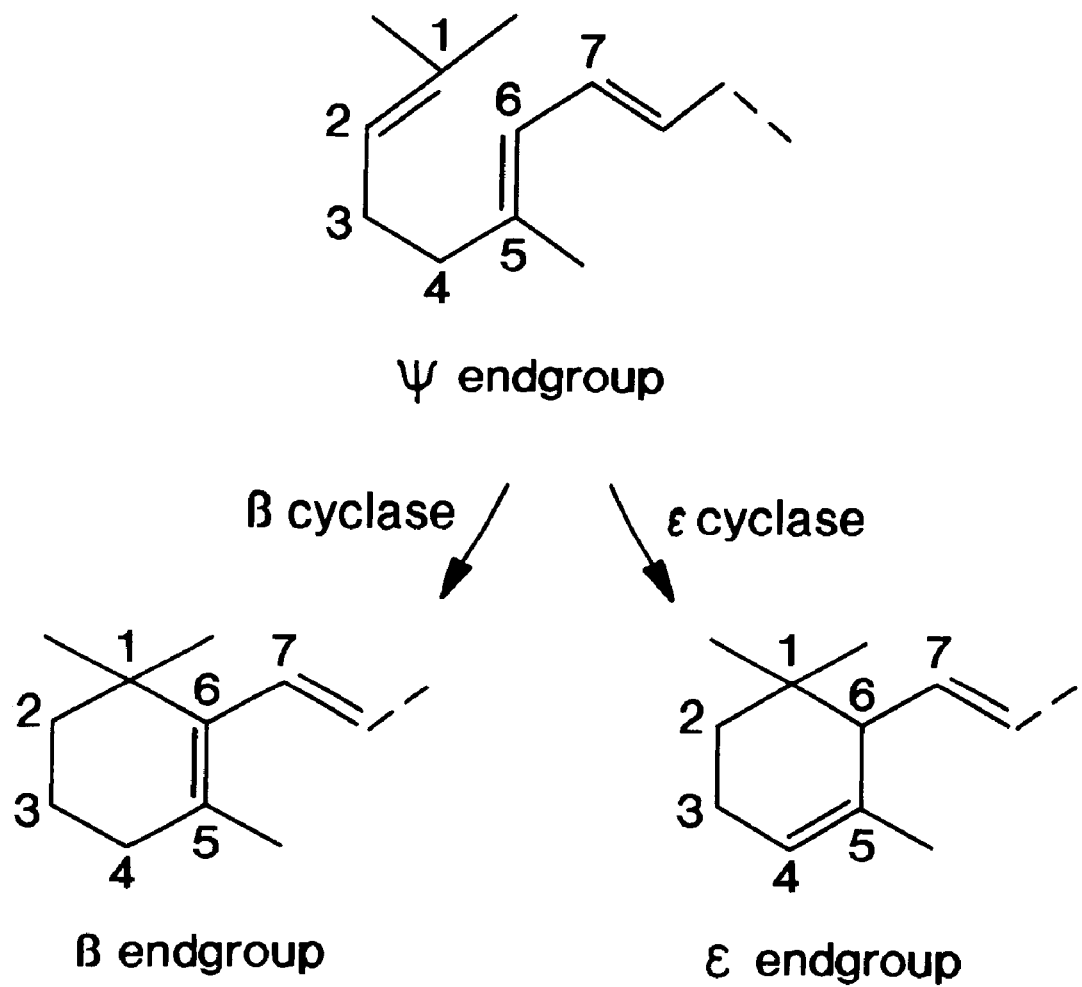
FIG. 2 is a flow diagram showing the reactions catalyzed by beta-cyclase and epsilon-cyclase.

Beta-cyclase cyclizes the termini of lycopene to form beta-rings. The reactions catalyzed by beta-cyclase or epsilon-cyclase are shown in FIG. 2.

Beta-carotene can then be converted to zeaxanthin by two sequential hydroxylation reactions catalyzed by beta-hydroxylase which adds hydroxyl groups to the number 3 carbons of each beta-ring.

Lycopene can also be converted to alpha-carotene through two sequential cyclization reactions, the first reaction is catalyzed by epsilon-cyclase which forms the intermediate delta-carotene which has an epsilon-ring at one terminus and the second reaction, catalyzed by beta-cyclase, cyclizes the other terminus to form a beta-ring. The reactions are shown in FIG. 1.

Alpha-carotene can be converted to alpha-cryptoxanthin in a reaction catalyzed by epsilon-hydroxylase which adds a hydroxyl group to the number three carbon of the epsilon-ring. A second hydroxylation reaction catalyzed by beta-hydroxylase converts alpha-cryptoxanthin to lutein by adding a hydroxyl group to the number three carbon of the beta-ring (FIG. 1).

In addition to converting lycopene to beta-carotene, beta-cyclase can convert neurosporene to beta-zeacarotene which is then converted by a desaturase to gamma-carotene. Gamma-carotene can then be converted to beta-carotene by beta-cyclase or alpha-carotene by epsilon-cyclase. Neurosporene can also serve as a substrate for epsilon-cyclase which converts it into alpha-zeacarotene which is then converted to delta-carotene by a desaturase. Beta-cyclase can further convert delta-carotene to alpha-carotene.

Beta-hydroxylase can also convert alpha-carotene to zeinoxanthin which can then be converted to lutein in a reaction catalyzed by epsilon-hydroxylase.

The complexity of the pathway and the diversity of products formed in the reactions catalyzed by beta-cyclase, epsilon-cyclase, beta-hydroxylase, and epsilon-hydroxylase indicates that the pathway can be engineered to produce specific carotenoid products by altering expression of any one or several of the abovementioned enzymes.

Thus, the object of the present invention is to produce genetically engineer marigold plants which preferentially overproduce a desired carotenoid pigment in the petal. The present invention provides transgenic marigold plants which contain at least one of the isolated DNAs encoding the carotenoid biosynthesis gene selected from the group consisting of beta-cyclase, epsilon-cyclase, beta-hydroxylase, IPP isomerase, epsilon-hydroxylase, and combinations thereof to produce a transgenic marigold which preferentially accumulates in the petal a specific carotenoid biosynthesis pigment. The present invention provides isolated DNAs encoding beta-cyclase, epsilon-cyclase, beta-hydroxylase and IPP isomerase from the marigold plant. The present invention also provides a method for transforming marigold plants with the isolated DNAs which encode at least one of the enzymes selected from the group consisting of beta-cyclase, epsilon-cyclase, beta-hydroxylase, IPP isomerase, epsilon-hydroxylase and combinations thereof to produce a marigold plant which preferentially accumulates a specific carotenoid pigment in the petal.

Thus, the present invention provides an isolated DNA encoding beta-cyclase (FIG. 3) wherein the isolated DNA has a sequence essentially the same as the sequence in SEQ ID NO:1 wherein the sequence between positions 304 to 1836 encodes an enzyme having an amino acid sequence (FIG. 4) essentially the same as the amino acid sequence in SEQ ID NO:2. The isolated DNA of marigold encoding beta-cyclase was cloned in the plasmid pBSIISK+ which was deposited under the terms of the Budapest Treaty at the American Type Culture Collection (ATCC), 12301 Parklawn Drive, Rockville, Md. 20852 on Jul. 28, 1999 as ATCC PTA-447.

The present invention also provides an isolated DNA sequence encoding beta-hydroxylase wherein the isolated DNA has a sequence (FIG. 7) essentially the same as the sequence in SEQ ID NO:3 wherein the sequence between positions 51 to 923 encodes an enzyme having an amino acid sequence (FIG. 8) essentially the same as the amino acid sequence in SEQ ID NO:4. The isolated DNA of marigold encoding beta-hydroxylase was cloned in the plasmid pBSIISK+ which was deposited under the terms of the Budapest Treaty at the ATCC on Jul. 28, 1999 as ATCC PTA-445.

The present invention further provides an isolated DNA sequence encoding epsilon-cyclase wherein the isolated DNA has a sequence (FIG. 5) essentially the same as the sequence in SEQ ID NO:5 wherein the sequence between positions 141 to 1688 encodes an enzyme having an amino acid sequence (FIG. 6) essentially the same as the amino acid sequence in SEQ ID NO:6. The isolated DNA of marigold encoding epsilon-cyclase was cloned in the plasmid pBSIISK+ which was deposited under the terms of the Budapest Treaty at the ATCC on Jul. 28, 1999 as ATCC PTA-446.

The present invention further provides an isolated DNA sequence encoding IPP isomerase wherein the isolated DNA has a sequence (FIG. 9) essentially the same as the sequence in SEQ ID NO:7 wherein the sequence between positions 101 to 796 encodes an enzyme having an amino acid sequence (FIG. 10) essentially the same as the amino acid sequence in SEQ ID NO:8. The isolated DNA of marigold encoding IPP isomerase was cloned in the plasmid pBSIISK+ which was deposited under the terms of the Budapest Treaty at the ATCC on Jul. 28, 1999 as ATCC PTA-448.

In a first embodiment of the present invention, a transgenic plant material is provided containing at least one isolated DNA encoding a marigold enzyme selected from the group consisting of beta-cyclase, beta-hydroxylase, and epsilon-cyclase wherein the isolated DNA is operably linked to a RNA promoter which in the plant produces an RNA that is antisense to the mRNA encoding the corresponding enzyme which is concurrently being produced by the plant. The isolated DNA, operably linked to a promoter to produce the antisense RNA, is selected from the group consisting of SEQ ID NO:1, preferably the sequence between positions 1 to 1836, SEQ ID NO:3, preferably the sequence between positions 1 to 923, and SEQ ID NO:5, preferably the sequence between positions 1 to 1688. The isolated DNA can range from 50 nucleotides to a length which corresponds to the length of the mRNA. In the preferred embodiment, the isolated DNA is operably linked to a promoter which is specific for transcription in the petal.

The present invention thus provides a method for producing a plant that preferentially accumulates either zeaxanthin, lycopene, alpha-carotene, beta-carotene, zeinoxanthin, or alpha-cryptoxanthin. The method comprises producing a transformed plant that contains a sequence selected from the group consisting of SEQ ID NO:1, preferably the sequence between positions 1 to 1836, SEQ ID NO.3, preferably the sequence between positions 1 to 923, SEQ ID NO:5, preferably the sequence between positions 1 to 1688 and combinations thereof, wherein the sequence is operably linked to a RNA promoter in the orientation which will produce an antisense RNA. The transformed plant produces the antisense RNA which inhibits the complementary mRNA (or pre-mRNA) produced by the plant that encodes the targeted carotenoid biosynthesis enzyme by forming a double-stranded RNA complex with the mRNA. The double-stranded complex is preferentially degraded by enzymes in the plant which are specific for double-stranded RNA thereby reducing the amount of the targeted mRNA. Since the concentration of mRNA encoding the targeted enzyme is reduced or eliminated, the quantity of the targeted enzyme product is reduced or eliminated which causes the preferential accumulation of those carotenoids that are substrates for the enzyme that is targeted.

Thus, in the method of the present invention for producing a plant that preferentially accumulates zeaxanthin, the isolated DNA encoding epsilon-cyclase is operably linked to a promoter in the orientation that in the transgenic plant is transcribed into an antisense RNA. The antisense RNA binds the mRNA that encodes epsilon-cyclase which prevents synthesis of the epsilon-cyclase enzyme. The inhibition of epsilon-cyclase synthesis causes a decrease in epsilon-cyclase in the plant which then causes the transformed plant to preferentially accumulate the carotenoid zeaxanthin.

In the method for producing a plant that preferentially accumulates lycopene, the transgenic plant contains the isolated DNA encoding epsilon-cyclase and the isolated DNA encoding beta-cyclase, operably linked to a promoter in the orientation which produces antisense RNA. The antisense RNAs bind the mRNAs encoding epsilon-cyclase and beta-cyclase, respectively, thereby preventing synthesis of the epsilon-cyclase and beta-cyclase enzymes. The decrease of the beta-cyclase and epsilon-cyclase enzymes causes the transformed plant to preferentially accumulate lycopene.

In the method for producing a plant that preferentially accumulates alpha-carotene, the transgenic plant contains the isolated DNA encoding epsilon-hydroxylase and the isolated DNA encoding beta-hydroxylase, operably linked to an promoter in the orientation which produces antisense RNA. The antisense RNAs bind to the complementary RNAs encoding epsilon-hydroxylase and beta-hydroxylase, respectively, preventing synthesis of epsilon-hydroxylase and beta-hydroxylase. The decrease of epsilon-hydroxylase and beta-hydroxylase causes the transformed plant to preferentially accumulate alpha-carotene.

In the method for producing a plant that preferentially accumulates beta-carotene, the transgenic plant contains the isolated DNA encoding epsilon-cyclase and the isolated DNA encoding beta-hydroxylase, operably linked to a promoter in the orientation which produces antisense RNA. The antisense RNAs bind their respective complementary mRNA which inhibits synthesis of the enzymes for beta-hydroxylase and epsilon-cyclase. The decrease of these enzymes causes the transformed plant to preferentially accumulate beta-carotene.

In the method for producing a plant that preferentially accumulates zeinoxanthin, the transgenic plant contains the isolated DNA encoding epsilon-hydroxylase, operably linked to a promoter in the orientation which produces antisense RNA. The antisense RNA binds the mRNA that encodes epsilon-hydroxylase which prevents synthesis of the epsilon-hydroxylase enzyme. The inhibition of epsilon-hydroxylase synthesis causes a decrease of the epsilon-hydroxylase in the plant which then causes the transformed plant to preferentially accumulate the carotenoid zeinoxanthin.

In the method for producing a plant that preferentially accumulates alpha-cryptoxanthin, the transgenic plant contains the isolated DNA encoding beta-hydroxylase, operably linked to a promoter in the orientation which produces antisense RNA. The antisense RNA binds the mRNA that encodes beta-hydroxylase which prevents synthesis of the beta-hydroxylase enzyme. The inhibition of synthesis causes a decrease of the enzyme in the plant which then causes the transformed plant to preferentially accumulate the carotenoid alpha-cryptoxanthin.

In the aforementioned embodiments, the promoter that is operably linked to the isolated DNA to make the antisense RNA is a promoter that causes the transcription of the RNA from the isolated DNA to occur specifically in the petal of the marigold. An example of an RNA promoter that is specific for transcription in the petal is the *Adonis vernalis* ketolase promoter.

The present invention provides a transgenic plant material containing one or more isolated DNAs encoding marigold enzymes selected from the group consisting of beta-cyclase, beta-hydroxylase, epsilon-hydroxylase, IPP isomerase and epsilon-cyclase wherein the beta-cyclase is encoded by the nucleotide sequence essentially homologous to the sequence between positions 1 to 1836 in SEQ ID NO:1, the beta-hydroxylase is encoded by the nucleotide sequence essentially homologous to the sequence between positions 1 to 923 in SEQ ID NO:3, the epsilon-cyclase is encoded by the nucleotide sequence essentially homologous to the sequence between positions 1 to 1688 in SEQ ID NO:5, the epsilon-hydroxylase and the IPP isomerase is encoded by the nucleotide sequence essentially homologous to the sequence between positions 1 to 796 in SEQ ID NO:7. The isolated DNA is operably linked to a promoter which in the host produces a functional mRNA that encodes the enzyme. In the preferred embodiment, the isolated DNA is operably linked to a promoter that is specific for transcription in the petal.

In another embodiment, the present invention provides a transgenic plant material containing combinations of isolated DNAs encoding marigold enzymes selected from the group consisting of beta-cyclase, beta-hydroxylase, epsilon-hydroxylase, IPP isomerase and epsilon-cyclase wherein a first isolated DNA sequence is operably linked to a promoter to produce antisense RNA and a second isolated DNA sequence is operatively linked to a promoter to produce an RNA that produces a functional enzyme. To produce the functional enzyme, the promoter is operably linked in the sense orientation to either beta-cyclase encoded by the nucleotide sequence essentially homologous to the sequence between positions 1 to 1836 in SEQ ID NO:1, the beta-hydroxylase encoded by the nucleotide sequence essentially homologous to the sequence between positions 1 to 923 in SEQ ID NO:3, the IPP isomerase encoded by the nucleotide sequence essentially homologous to the sequence between positions 1 to 796 SEQ ID NO:7, the epsilon-hydroxylase or the epsilon-cyclase encoded by the nucleotide sequence essentially homologous to the sequence between positions 1 to 1688 in SEQ ID NO:5. To produce the antisense RNA, the isolated DNA is operably linked to the promoter in the antisense orientation and the length of the isolated DNA can range from 50 nucleotides to a length which corresponds to the full length of the mRNA. In the preferred embodiment, the isolated DNA is operably linked to a promoter that is specific for transcription in the petal.

Thus, the present invention provides a means for manipulating the carotenoid pathway in a plant to overproduce specific carotenoids and repress production of other carotenoids. For example, the present invention provides a means for inhibiting synthesis of epsilon-cyclase by introducing into the plant, DNA encoding RNA antisense to the epsilon-cyclase mRNA produced by the plant. Inhibition of epsilon-cyclase by the hybridization of the antisense RNA to the mRNA prevents synthesis of epsilon-cyclase which then reduces or prevents the conversion of neurosporene to alpha-zeacarotene, lycopene to delta-carotene, and gamma-carotene to alpha-carotene. Therefore, the carotenoid biosynthetic pathway will preferentially proceed towards the production of zeaxanthin. Inhibiting beta-hydroxylase in the same manner will prevent conversion of beta-carotene to zeaxanthin, and zeinoxanthin to lutein thereby causing the accumulation of beta-carotene and zeinoxanthin.

In a second example according to the present invention, inhibition of the synthesis of the beta-cyclase and epsilon-cyclase enzymes is accomplished by introducing into the plant DNA encoding RNAs antisense to the beta-cyclase and epsilon-cyclase mRNAs produced by the plant. The antisense RNAs bind to their respective complementary mRNAs which inhibits translation of their respective mRNAs, thereby inhibiting synthesis of the beta-cyclase and epsilon-cyclase enzymes. The inhibition of the synthesis of the beta-cyclase and epsilon-cyclase enzymes reduces or eliminates conversion of neurosporene to beta-zeacarotene and lycopene to beta-carotene or delta-carotene. Therefore, the primary product of the carotenoid in a pathway is lycopene.

In a third example according to the present invention, inhibition of synthesis of the beta-hydroxylase and epsilon-hydroxylase enzymes will cause the preferential accumulation of alpha-carotene. It also follows from this example that inhibition of beta-hydroxylase according to the present invention prevents alpha-cryptoxanthin from being converted to lutein, thereby causing accumulation of alpha-cryptoxanthin, and that inhibition of only epsilon-hydroxylase prevents zeinoxanthin from being converted to lutein, thereby causing accumulation of zeinoxanthin.

The present invention also provides for manipulation of the carotenoid biosynthesis pathway wherein any one of the abovementioned enzymes is overproduced in the plant. For example, overproduction of beta-cyclase according to the present invention will produce an excess of beta-cyclase which will more effectively compete with epsilon-cyclase for neurosporene and lycopene substrates thereby causing the carotenoid biosynthesis pathway to preferentially increase production of beta-carotene and zeaxanthin, and decrease production of alpha-carotene and its derivatives. Conversely, overproduction of epsilon-cyclase will cause the carotenoid biosynthesis pathway to shift towards production of alpha-carotene and its derivatives. Therefore, the present invention encompasses manipulation of the carotenoid biosynthesis pathway by providing to the plant, an isolated DNA containing at least one of the enzymes selected from the group consisting of beta-cyclase, beta-hydroxylase, epsilon-cyclase and epsilon-hydroxylase which when transcribed into mRNA and translated in the plant, provides an additional amount of the carotenoid biosynthesis enzymes selected to be overproduced.

The genes encoding beta-cyclase, epsilon cyclase and beta-hydroxylase were isolated from marigold and cloned into a bacterial plasmid. The DNA sequence for beta-cyclase is shown in FIG. 3. The gene encoding the beta-cyclase is 1533 bp and corresponds to nucleotide position 304 to 1836. The amino acid sequence for beta-cyclase is shown in FIG. 4. The DNA sequence for epsilon-cyclase is shown in FIG. 5. The gene encoding the epsilon-cyclase is 1548 bp and corresponds to nucleotide position 141 to 1688. The amino acid sequence for epsilon-cyclase is shown in FIG. 6. The DNA sequence for beta-hydroxylase is shown in FIG. 7. The gene encoding the beta-hydroxylase is 873 bp and corresponds to nucleotide position 51 to 923. The amino acid sequence for beta-cyclase is shown in FIG. 8. The DNA sequence for IPP isomerase is shown in FIG. 9. The gene encoding for IPP isomerase is 796 bp and corresponds to nucleotide positions 101 to 796. The amino acid sequence for IPP isomerase is shown in FIG. 10. The petal specific promoter was isolated from *Adonis vernalis* and is the promoter regulating the ketolase gene. The marigold genes encoding geranylgeranyl pyrophosphate synthase and zeta-carotene desaturase have been cloned and sequenced.

Construction of clones containing the carotenoid biosynthesis DNA operably linked to a promoter can be accomplished using techniques well known in the art (for example Sambrook et al., *Molecular Cloning: A Laboratory Manual*, Cold Spring Harbor Laboratory, Cold Spring Harbor, N.Y. 1989). Suitable vectors for eukaryote expression in plants are described in Frey et al, (1995) Plant J., vol. 8 pp. 693- and Misawa et al, (1994) Plant J., vol. 6, pp. 481–489 which are incorporated herein by reference.

Transgenic plants are constructed which contain the DNA sequences comprising the present invention. The incorporation of these sequences into the plant allows the carotenoid biosynthetic pathway to be manipulated to produce specific carotenoids. The manipulation can be by antisense inhibition, overproduction of selected carotenoid biosynthesis enzymes, or a combination thereof.

There are many methods known in the art for transforming a plant cell. Common methods include transformation with T-DNA containing the DNA of interest and using *Agrobacterium tumefaciens* as the means for transformation or with Ti or Ri plasmids using the bacterium *A. rhizogenes* as the means for transformation. A suitable plasmid for transformations is the pART27/7 plasmid vector isolated from *Agrobacterium tumefaciens*. Other methods for transforming a plant cell include cell fusion, electroporation, biolistic or conventional injection.

Agrobacterium related methods require special plasmid vectors such as intermediate or binary vectors. Intermediate vectors require integration into Ti or Ri plasmids by homologous recombination into the region containing the T-DNA. The intermediate vector is transferred into the Agrobacterium by means of conjugation in the presence of a helper plasmid. The transformed Agrobacterium is then used to transform the cell. The preferred method for transforming Agrobacterium is using plasmids of the binary type. Binary vectors replicate both in *Escherichia coli* and Agrobacterium. Therefore, these vectors containing the desired DNA can be constructed using conventional molecular biology techniques and the recombinant plasmid directly transferred to Agrobacterium. Binary vectors usually contain a marker gene and a polylinker for inserting the desired DNA flanked by the left and right T-DNA border regions. Both the intermediate and binary vectors contain the vir region which is necessary for transfer of the T-DNA into the plant cell.

Transformation of plant cells with transformed Agrobacterium is by co-cultivation of the cells with the transformed Agrobacterium which results in transfer of the T-DNA containing the desired DNA into the plant cell. Sources for plant cells are explants which can include but is not limited to sections of leaves, stems, roots, segments of petioles, flowers and flower parts, and cotyledon tissue. Whole plants are regenerated from the infected plant material or from protoplasts or suspension-cultivated cells in a suitable medium which can contain antibiotics or biocides (e.g., kanamycin, bleomycin, hygromycin, chloramphenicol) for selection of the transformed plant cells. The ability and efficiency of regenerating a transformed or transgenic plant using transformed isolated cells or explants is dependent on the species of plant and the type of transformed cell. Transformation of marigold tissue can be achieved according to the Agrobacterium-mediated method for transforming plants disclosed in U.S. Pat. No. 5,684,238 to Ausich et al and U.S. Pat. No. 5,618,988 to Hauptmann et al which are herein incorporated by reference.

Non-Agrobacterium mediated transformation such as electroporation, injection, cell fusion, or particle bombardment do not require special plasmids and can therefore use standard plasmids such as the pUC derivatives and conventional cloning techniques. For example, to make the transgenic marigold plants of the present invention using the Biolistic bombardment method, marigold tissue is transformed using the Biolistic method described in U.S. Pat. No. 5,767,368 to Zhong et al which is herein incorporated by reference. Further examples of the Biolistic bombardment method are disclosed U.S. Pat. No. 5,736,369 to Bowen et al which is herein incorporated by reference.

Expression of cloned DNAs such as the isolated DNAs of the present invention in the plant cell requires the isolated DNA to be operably linked to a promoter. The preferred promoter is the petal specific promoter from the ketolase gene of and *Adonis vernalis* (pheasant's eye). Examples of other promoters which are useful are viral promoters such as the cauliflower mosaic virus 35S promoter, heat shock protein promoters such as the HSP70 promoter, light induced promoters such as the ST-Lsl or the rubisco small subunit promoter, stress response promoters such as the PR promoter, the *Agrobacterium tumefaciens* nos promoter, and various organ, root, tuber, leaf, and other flower specific promoters. Examples of other promoters contemplated are differentially regulated promoters which are promoters that operate in only certain plant tissues, under certain environmental conditions or at a particular developmental stages of the plant. The CRB promoter isolated from the CRB gene of the 12S seed protein of *Arabidopsis thaliana* which targets expression to the seed is one such differentially regulated promoter. The DRE promoter element that is inducible under stress is an example of a plant promoter that responds to environmental conditions (Yamaguchi-Shinozaki et al, Plant Cell 6:251–264 (1994)). The isolated DNA also requires being operably linked to a transcription termination signal. The termination signal can be the sequence naturally associated with the isolated DNA or can be a sequence operably linked to the 3' end of the isolated DNA. An example of such a sequence is the transcription termination signal of the octopine synthase gene.

In the embodiments of the invention wherein antisense RNA production is desired, the transcription of the isolated DNAs in the plant cell produces an RNA that is antisense to the mRNA or pre-mRNA of the gene product targeted for inhibition. James (Antiviral Chem. Chemotherapy, 2:191–214 (1991)) has reviewed antisense RNA and its use in gene inhibition therapy. Other reviews of antisense technology specifically directed to transgenic plants are by Senior (Biotechnol. Genet. Rev., 15:79–119 (1998)) and Nellen et al (Mol. Biotechnol., 6:7–15 (1996)). Generally, the inhibition is affected in the cell nucleus by the formation of a double-stranded RNA consisting of one molecule of antisense RNA and one molecule of the mRNA forming a double helix molecule. The double helix molecule is preferentially degraded in the nucleus by enzymes that specifically degrade double-stranded RNA molecules. In this manner, the pool of mRNA available for translation is reduced or eliminated which in turns reduces the pool of enzyme encoded by the mRNA. The length of the antisense RNA that is effective for inhibition is between 50 nucleotides and a size which corresponds to the full length of the mRNA it is complementary with. The degree of inhibition affected by the present invention ranges from 70% to 90% with a maximum of approximately 98%, depending on the length of the antisense RNA and the particular region of the mRNA it is directed to when the antisense RNA is shorter than the mRNA. Thus, the present invention provides a method for substantially inhibiting a particular enzyme by using an RNA that is antisense to the enzymes mRNA.

The present invention describes transgenic marigold plants wherein the carotenoid biosynthesis pathway is manipulated to produce specific carotenoids by transforming marigold tissue with various combinations of one or more isolated DNAs containing beta-cyclase, epsilon-cyclase, beta-hydroxylase, IPP isomerase or epsilon-hydroxylase in either antisense or sense orientation. However, manipulation of the carotenoid pathway according to the present invention can include other enzymes that are involved in the biosynthesis of carotenoids. These enzymes can be of marigold origin or from other organisms. Examples of such genes are the 1-deoxy-D-xylulose 5-phosphate synthase (DXP synthase) from *E. coli* (GenBank Accession No. U82664), the marigold homolog to the DXP synthase which produces a deep red when in the presence of lycopene, and the *Arabidopsis thaliana* homolog to DXP synthase (Cla 1 gene—GenBank Accession No. U27099). Thus, the present invention is not limited to the specific genes mentioned herein but also includes other genes encoding enzymes that are involved in carotenoid biosynthesis.

The following examples are intended to promote a further understanding of the present invention.

EXAMPLE 1

HPLC characterization of selected marigold lines including known color variants was performed to identify marigold color variants that had mutations in the carotenoid biosynthetic pathway. These mutations were expected to accumulate intermediates such as beta or alpha carotene or mono-hydroxy derivatives.

Normal orange marigold lines contain between 90 and 98% lutein. The vast majority of the lutein is esterified to fatty acids. HPLC analysis was performed on all commercially available marigold color variants such as the dark orange, red fringed, yellow, cream, and white variants among others. All the commercially available variants were identified as quantitative mutants, that is these variants accumulated less of each intermediate in the same proportion. In other words, none of the variants accumulated any intermediate at appreciable levels. Therefore, marigold variants that have useful carotenoid mutations that cause accumulation of carotenoid biosynthetic pathway intermediates appeared to be distant.

EXAMPLE 2

A cDNA library was constructed to screen for and isolate cDNAs encoding enzymes involved in the carotenoid biosynthetic pathway. To facilitate construction of the cDNA library, the mRNA levels for carotenoid biosynthetic steps during marigold flower development was analyzed to identify the appropriate stage of development to prepare the cDNA library. The cDNAs targeted were cDNAs encoding beta-cyclase, epsilon-cyclase, beta-hydroxylase, IPP isomerase and epsilon hydroxylase. It was also discovered that the corresponding cDNAs encoding beta-cyclase, epsilon-cyclase, and beta-hydroxylase from *Arabidopsis thaliana* hybridized to the corresponding marigold genes. This discovery enabled expression of the abovementioned carotenoid pathway mRNAs be directly evaluated during floral development.

Based on the analysis of mRNA levels, three of six arbitrary marigold floral development stages were selected for sources of RNA for library construction. A cDNA library containing more than $10^7$ independent cDNAs was constructed and screened for cDNAs encoding beta-cyclase, epsilon-cyclase, beta-hydroxylase, and epsilon-hydroxylase. Briefly, poly(A+) RNA was isolated from developing marigold flowers and made into cDNA using art known methods. A cDNA library was made by Stratagene (La Jolla, Calif.) using the Stratagene Lambda ZAP Cloning System. The library was non-directional in the vector and consisted of more than $10^7$ independent clones. Various screening procedures were used including heterologous screening using relevant Arabidopsis genes, functional screening based on color complementation and novel methods based on accelerated growth at low temperature. Identification of clones containing carotenoid biosynthesis enzymes was as follows.

Marigold beta-cyclase was identified by color complementation of a lycopene accumulating E. Coli strain. This method is described in U.S. Pat. No. 5,744,341 to Cunningham, Jr. et al which is herein incorporated by reference. Approximately 360,000 colonies were screen. Of these colonies, 4 yellow colonies were picked, and DNA was extracted from two of the colonies and the DNA sequenced. FIG. 3 shows the DNA sequence for the marigold beta-cyclase. The amino acid sequence for beta-cyclase was deduced from the DNA sequence and is shown in FIG. 4.

Marigold epsilon-cyclase was identified by plaque hybridizations using as the probe the *Arabidopsis thaliana* epsilon-cyclase (GenBank Accession No: U50738). A DNA clone containing an epsilon cyclase from *Arabidopsis thaliana* that is suitable for use as a probe to screen the library is available from the ATCC as ATCC-98005. Approximately 280,000 plaques were screened and 9 plaques were purified. DNA was isolated from 2 of the plaques and the DNA was sequenced. The DNA sequence is shown in FIG. 5. The amino acid sequence for epsilon-cyclase was deduced from the DNA sequence and is shown in FIG. 6.

Marigold beta-hydroxylase was identified by plaque hybridizations using as the probe the Arabidopsis beta-hydroxylase. A DNA clone suitable for use as a probe to screen the library is available from the ATCC as ATCC-98003. Approximately 280,000 plaques were screened and 13 plaques were purified. DNA was isolated from 3 plaques and the DNA was sequenced. The DNA sequence is shown in FIG. 7. The amino acid sequence for beta-hydroxylase was deduced from the DNA sequence and is shown in FIG. 8.

Marigold IPP isomerase was identified by using a cold screen method in which zeaxanthin expressing *E. coli* were transformed with the marigold cDNA library and grown at 18° C. Rapidly growing pigmented colonies were which contained the IPP isomerase were characterized. Five independent colonies were further shown to contain marigold IPP isomerases. Four of these clones were partially sequenced and one of these clones was fully sequenced. All of these clones were closely related but not identical. The DNA sequence is shown in FIG. 9. The amino acid sequence for IPP isomerase was deduced from the DNA sequence and is shown in FIG. 10.

Clones from a marigold cDNA library encoding geranylgeranyl pyrophosphate synthase and zeta-carotene desaturase have been identified by homology to their homologous genes in Arabidopsis. These genes have been isolated and sequenced.

EXAMPLE 3

Regeneration of marigold plants is a key element for successful generation of transgenic plants, however there is little information regarding tissue culture of marigold. Therefore, the objective of this example was to develop a method for the regeneration of marigold in vitro. As part of our objective, several commercial and proprietary marigold genotypes were evaluated for germination and growth in culture.

Identification of marigold genotypes that regenerated best in vitro was performed by evaluating the number of adventitious shoots per experiment. All varieties of marigold plant tissue were evaluated.

Regeneration potential of marigold was evaluated by monitoring the morphological response of marigold tissues to various hormonal concentrations and combinations. Regeneration was evaluated in three stages: shoot induction, shoot elongation, and rooting. The first stage, shoot induction, was performed as follows. The media was Murashige and Skoog (MS) medium containing various concentration of benzyladenine (BA) ranging from 1.0 mg/l to 5.0 mg/l. At each concentration of BA, various concentrations of IAA was added, ranging from 0.5 mg/l to 5.0 mg/l. Table 1 shows that MS media containing 5.0 mg/l BA and 3.0 mg/l IAA was the best medium for regenerating transformed marigold cultures.

TABLE 1

| MEDIA | | TISSUE RESPONSE |
|---|---|---|
| BA (1.0 mg/l) | IAA (1.0 mg/l) | R– |
| | IAA (3.0 mg/l) | R–S– |
| | IAA (5.0 mg/l) | C+ |
| BA (3.0 mg/l) | IAA (1.0 mg/l) | S++, R–, C+ |
| | IAA (3.0 mg/l) | S++ |
| | IAA (5.0 mg/l) | S+, C+ |
| BA (5.0 mg/l) | IAA (1.0 mg/l) | S++, C+ |
| | IAA (3.0 mg/l) | S+, C+ |
| | IAA (5.0 mg/l) | S–, R+, C+ |
| BA (1.0 mg/l) | IAA (0.5 mg/l) | S+, C++ |
| BA (5.0 mg/l) | IAA (3.0 mg/l) | S+++, R+, C++ |

R = roots, S = shoots, C = callus
+++ = excellent development; ++ = very good development; + = good development; – = poor development Shoot buds, differentiated as above, are subcultured in the same media as above every two weeks for multiplication of shoots, as long as the regeneration from callus continues. Once shoots are visible from callus or original explants they are subcultured to MS media containing one tenth of the hormones used for shoot induction.

In the next stage, shoot elongation, shoot buds from above are subcultured on MS media without BA and IAA. In the final stage, rooting, the tissue from the shoot elongation stage is further subcultured in media without BA and IAA.

Table 2 summarizes the response of different marigold explants to media containing different hormones.

TABLE 2

| MARIGOLD VARIETY | MORPHOGENIC RESPONSE | STATUS |
|---|---|---|
| CLIMAX HYBRID TOREADOR (1) | S+, R+, C+, NGR+ | |
| GOLDEN CLIMAX HYBRID | S++, R++, C+, NGR++ | |
| XANTHOPHYLL SCARLETADE | S+, C++ | |
| XANTHOPHYLL ORANGEADE | S+, C++ | |
| XANTHOPHYLL DEEP ORANGE | S+, C++ | |
| 032-442 (5287) | S-, C++, NGR++ | leaf, stem, cotyledon |
| 032-439 (1273) | S++, R++, C++, NGR- | leaf, stem, cotyledon |
| 36969 | S++, R++, C++, NGR- | cotyledon |
| 36898 | S++, R++, C++, NGR- | cotyledon |
| 032-440 (1274) | S+, R-, C++, NGR- | cotyledon |

R = roots, S = shoots, C = callus, NGR = negative geotropic roots
+++ = excellent development; ++ = very good development; + = good development; − = poor development There were recurring problems with most genotypes which was manifested as browning of the tissue and growth of non-geotropic roots (Growth of roots can be a problem during regeneration, because once the roots start to form, the growth of other plant structures decreases). However, in terms of regeneration of marigold plants from untransformed tissue, many plants have been regenerated from different explants, tissues and genotypes according to the method shown herein.

EXAMPLE 4

Initial marigold tissue culture transformations were performed to determine the appropriate tissue for transformation with Agrobacterium and then plant regeneration from transformed tissue. The Agrobacterium that was used was Agrobacterium LB4404 containing in most cases the transformation vector pBI121 which contained the CaMV 35S promoter driving the beta-glucuronidase reporter gene (GUS) and the NPTII gene as the selectable marker. The beta-glucuronidase cleaves the colorless substrate, X-glu, producing a product having a blue color.

Leaves were selected as the tissue from marigold for transformation because leaves are generally an easy regenerating tissue providing healthy plants back from leaves in culture after approximately eight to six weeks. Large scale transformations were initiated in earnest using six Pan American marigold lines in case there were cultivar variations as in tomato which would affect transformation. Over 5,000 independent leaf sections were individually transformed by Agrobacterium-mediated transformation and carried through regeneration attempts for approximately eight to twelve weeks, with weekly or bi-weekly transfers for each transformation event. Despite the number of transformations not a single transformation event scored as transformed plantlets were ever identified even though transformed callus tissue that proliferated roots could be obtained. However, the transformed callus tissue was recalcitrant to plant regeneration.

It was observed that during these transformation attempts, many of the transformed tissues turned brown, would not show any response to hormones, and eventually died. Several alternative approaches were tried to transform marigold leaf tissue. Among them being using different tissues for transformation, and using other strains of Agrobacteria as the transforming agent. Because marigolds produce thiophenes which are natural antibacterial compounds and may inhibit Agrobacterium-mediated transformation, transformants were co-cultivated in the dark (light activates thiophenes), transformations were performed with low thiophene producing strains of marigolds, or transformants were co-cultivated in sulfate deficient media (to decrease thiophene production in vitro). None of these variations produced transformed plants. Therefore, the conclusion was that despite the ability of marigold leaf tissue to regenerate better than any other plant tissue, marigold leaves were difficult to transform (less than 1% efficiency) and the tissue that was transformed could not be made to regenerate into plants.

Since marigold leaves were refractory to regeneration after transformation, other marigold tissue was evaluated for regeneration and transformation. Marigold cotyledon tissue was tested for ability to be transformed. Cotyledon tissue was transformed with Agrobacterium LB4404. Transformed cotyledon tissue is capable of transformation several independent transformation events have produced transformed plants capable of growth in soil.

The protocol for marigold transformation that was developed using Agrobacterium is set forth below.

Induction and inoculation. Two weeks prior to the experiment, germinate seeds aseptically in MS media and agar plates. Two days prior to inoculation, cut off cotyledons from seedlings and place them on MS media containing hormones as described in Example 3, and incubate under standard conditions. One to two days prior to inoculation, streak *Agrobacterium tumefaciens* onto a petri plate containing LB agar and grow for two days with appropriate antibiotics.

On day of inoculation, scrape the new growth bacteria from the culture plate and make a mixture using induction medium in MS media. Shake the mixture for 30 minutes before using. Using sterile forceps transfer all cotyledons to a plate and then add the bacteria mixture and vacuum infiltrate for 5 minutes. Then remove all explants from the bacteria mixture and place the bacteria coated explants back into the same media they had been growing in for co-cultivation. The co-cultivation period allows the bacteria and plant material to remain in close proximity for 2 to 3 days. After the co-cultivation period, transformed plant tissue is selected by transferring all the explants to the same media containing antibiotics to kill the Agrobacterium and kanamycin or hygromycin to select for transformants. Transformants can also be selected for herbicide resistance, provided that the transformed tissue is co-transformed with DNA encoding a herbicide resistance gene and the selection is performed in media containing the herbicide. Regeneration is essentially as described in Example 3.

The following three transformation experiments were done using the 35S-GUS-HYG construct (similar to pBI121 except encoding resistance to the antibiotic hygromycin) in LB4404. The explant used was cotyledons from aseptically grown marigold seedlings for each genotype. Regeneration was essentially as described in Example 3. The results shown in Table 3, demonstrate that using the transformation conditions and regeneration conditions described herein, cotyledon tissue from marigolds can be transformed and regenerated into plants. This important discovery provides both the method and transgenic marigold of the present invention.

TABLE 3

| Variety | No. Explants inoculated | Transformants GUS positive | Total plantlet clones (after subculture) |
|---|---|---|---|
| 032-439 (1273) | 320 | 6 | 48 |
| 36969 | 300 | 5 | 28 |
| 36969 | 350 | 4 | 25 |

The use of cotyledons allowed plantlets to be regenerated following inoculation with Agrobacterium. Even thought the transformation efficiency of cotyledon was not much better than the efficiency for transforming leaves, the transformed cotyledon tissue is capable of being regenerated into plants. Currently, there are two transformed plants from transformed 032–439 in the soil. There is one transformed 36969 plant in the soil with several others ready for planting. Thus, the method developed herein will produce transgenic marigold plants from transformed cotyledon tissue.

EXAMPLE 5

As an alternative to Agrobacterium mediated transformation, each transformation of the nuclear genome of marigold is accomplished by transforming marigold tissue such as cotyledon tissue or shoot-tips with one of the three isolated DNAs. The DNAs are co-precipitated onto 1.0 $\mu$m tungsten particles according to the method described by Zhong et al. (Plant Physiology, 110:1097–1107 (1996)). Transformation by Biolistic bombardment is performed as disclosed in U.S. Pat. No. 5,320,961 to Zhong et al.

Multiple marigold shoot-tip clumps are initiated from shoot tips of marigold seedlings and maintained in light for 4-week intervals on Murashige and Skoog (MS) medium containing 2 mg/ml benzyladenine (BA) and 0.5 mg/L 2,4-dichlorophenoxyacetic acid (2,4-D). Shoot tips and shoot clumps are physically exposed by removal of the leaves, when necessary, and placed in a circular area having a diameter of approximately 1.5 cm prior to transformation. Alternatively, cotyledon tissue can be transformed by Biolistic bombardment.

Transformation consists of bombarding the shoot tips and clumps with the tungsten particles coated with the DNA precipitate using a Biolistic particle acceleration device (PDS 1000/He, Bio-Rad, Hercules, CA USA) under a chamber pressure of 26 mm of Hg at distances of 1.5, 2.0 and 6.5 cm from the rupture disc to the macrocarrier to the stopping screen to the target, respectively, with a density of 150 ug/shot of the coated tungsten particles with 4 shots and 1,550 p.s.i. acceleration pressure.

Afterwards, the bombarded tissue is cultured on MS medium containing 2 mg/ml BA and 0.5 mg/L 2,4-D for 6 to 8 weeks. This important step is necessary to reduce the degree of chimerism in the transformed tissue. Afterwards, the green clumps are selected, divided and subcultured in the above medium. Then, those plantlets that have normal root development are transferred to pots and acclimated to soil conditions before being transferred to greenhouses.

Production of specific carotenoid compounds is determined using methods described in Example 1. In addition, a selection method such as antibiotic resistance (Example 5) or herbicide resistance can be incorporated into this method by co-transforming the plant tissue an isolated DNA that encodes for antibiotic resistance or herbicide resistance and cultivating the transformed tissue in the presence of the antibiotic or herbicide.

EXAMPLE 6

To make a transgenic marigold plant containing an isolated DNA that contains a DNA sequence from the beta-cyclase gene as shown in SEQ ID NO:1, marigold cotyledon tissue is transformed as in Example 4 or 5. The transformed tissue is used to make the transgenic plant. The DNA sequence produces RNA in the antisense orientation.

EXAMPLE 7

To make a transgenic marigold plant containing an isolated DNA that contains a DNA sequence from the beta-hydroxylase gene as shown in SEQ ID NO:3, marigold cotyledon tissue is transformed as in Example 4 or 5. The transformed tissue is used to make the transgenic plant. The DNA sequence produces RNA in the antisense orientation.

EXAMPLE 8

To make a transgenic marigold plant containing an isolated DNA that contains a DNA sequence encoding the epsilon-cyclase gene as shown in SEQ ID NO:5, marigold cotyledon tissue is transformed as in Example 4 or 5. The transformed tissue is used to make the transgenic plant. The DNA sequence produces RNA in the antisense orientation.

EXAMPLE 9

To make a transgenic marigold plant containing an isolated DNA that contains a DNA sequence from the beta-cyclase gene as shown in SEQ ID NO:1, marigold cotyledon tissue is transformed as in Example 4 or 5. The transformed tissue is used to make the transgenic plant. The DNA sequence produces RNA in the sense orientation which encodes beta-cyclase.

EXAMPLE 10

To make a transgenic marigold plant containing an isolated DNA that contains a DNA sequence from the beta-hydroxylase gene as shown in SEQ ID NO:3, marigold cotyledon tissue is transformed as in Example 4 or 5. The transformed tissue is used to make the transgenic plant. The DNA sequence produces RNA in the sense orientation which encodes beta-hydroxylase.

EXAMPLE 11

To make a transgenic marigold plant containing an isolated DNA that contains a DNA sequence encoding the epsilon-cyclase gene as shown in SEQ ID NO:5, marigold cotyledon tissue is transformed as in Example 4 or 5. The transformed tissue is used to make the transgenic plant. The DNA sequence produces RNA in the sense orientation which encodes epsilon-cyclase.

EXAMPLE 12

To make a transgenic marigold plant containing an isolated DNA that contains a DNA sequence from the IPP isomerase gene as shown in SEQ ID NO:7, marigold cotyledon tissue is transformed as in Example 4 or 5. The transformed tissue is used to make the transgenic plant. The DNA sequence produces RNA in the sense orientation which encodes IPP isomerase.

EXAMPLE 13

Transgenic marigold plants containing more than one isolated DNA containing a carotenoid biosynthesis synthesis gene in either the antisense or the sense orientation is made by crossing-breeding the transgenic plants (made according to Examples 6 to 12) which contain isolated DNA containing the sequence from SEQ ID NO:1, SEQ ID NO:3 or SEQ ID NO:5 according to methods well known in the art such as those provided in (Zhang et al, Theor. Appl. Genet. 92:752–761, (1996); Zhong et al, Plant Physiol. 110:1097–1107, (1996); Zhong et al, Planta, 187:483–489, (1992)). Transgenic plants that carry a low copy number of the isolated DNA used for cross-breeding.

Briefly, transgenic marigold plants that contain more than one isolated DNA are made by first making transgenic plants that contain either SEQ ID NO:1, SEQ ID NO:3, SEQ ID NO:5 or SEQ ID NO:7 to make a first, a second, a third and a fourth transgenic plant. The first and second transgenic plants are cross-bred to create a bi-transgenic plant (contains SEQ ID NO:1 and SEQ ID NO:3) which can then cross-bred with the third transgenic plant to make a tri-transgenic plant which contains isolated DNAs containing SEQ ID NO:1, SEQ ID NO:3, and SEQ ID NO:5. The fourth transgenic plant can be crossed with the tri-transgenic plant to produce the quadri-transgenic plant containing SEQ ID NO:1, SEQ ID NO:3, SEQ ID NO:5 and SEQ ID NO:7. In the above described manner, transgenic plants containing any combination and any number of isolated DNAs can be constructed.

Transgenic plant lines containing more than one isolated DNA are cross-pollinated with transgenic plant lines containing another isolated DNA. The resulting hybrid progeny are cross-pollinated with transgenic plant lines containing other isolated DNAS. Each transgenic plant line produces specific carotenoid compounds depending on both what isolated DNAs are contained by the plant and whether the DNAs express RNA in the antisense orientation, the sense orientation or a combination thereof.

Alternatively, transgenic plants containing more than one type of isolated DNA can be made by multiple transformations. For example, cotyledon tissue from a transgenic plant containing one of the isolated DNAs can be transformed with another of the isolated DNAs to produce the bi-transgenic plant as shown in Examples 4 to 5.

Another alternative for making transgenic plants containing more than one type of isolated DNA is to either simultaneously transform the cotyledon tissue with multiple isolated DNAs containing the desired gene sequences or transform with one isolated DNA that contains each desired gene sequence. Transformation can be as shown as in Examples 4 to 5.

EXAMPLE 14

Transgenic marigold plants containing an isolated DNA which contains more that one DNA sequence that produces antisense RNA to mRNA encoding at least two of beta-cyclase, beta-hydroxylase, or epsilon-cyclase are produced by a single transformation as shown in Example 4 or 5. The isolated DNA in this example contains DNA sequences from a combination of at least two DNA sequences selected from the group of DNA sequences which encodes beta-cyclase, beta-hydroxylase, or epsilon-cyclase wherein the DNA sequences are in the antisense orientation.

EXAMPLE 15

Transgenic marigold plants containing an isolated DNA which contains more that one DNA sequence that produces sense RNA encoding at least two of beta-cyclase, beta-hydroxylase, IPP isomerase or epsilon-cyclase are produced by a single transformation as shown in Example 4 or 5. The isolated DNA in this example contains DNA sequences from a combination of at least two DNA sequences selected from the group of DNA sequences which encodes beta-cyclase, beta-hydroxylase, IPP isomerase or epsilon-cyclase.

EXAMPLE 16

Transgenic marigold plants containing an isolated DNA which contains at least one DNA sequence that produces sense RNA encoding at least one of beta-cyclase, beta-hydroxylase, IPP isomerase, or epsilon-cyclase and at least one DNA sequence which produces antisense RNA to mRNA encoding at least one of beta-cyclase, beta-hydroxylase or epsilon-cyclase are produced by a single transformation as shown in Example 4 or 5. The isolated DNA in this example contains (1) a DNA sequence from at least one DNA sequence selected from the group of DNA sequences which encodes beta-cyclase, beta-hydroxylase, or epsilon-cyclase, and (2) a DNA sequence in the antisense orientation from at least one DNA sequence not selected in (1).

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. An isolated DNA comprising a DNA sequence encoding marigold beta-cyclase.

2. The isolated DNA of claim 1 comprising the DNA sequence of SEQ ID NO:1.

3. The isolated DNA of claim 1 wherein the beta-cyclase comprises the amino acid sequence of SEQ ID NO:2.

4. A transgenic plant comprising an isolated DNA encoding marigold beta-cyclase.

5. The transgenic plant of claim 1 wherein the isolated DNA comprises the nucleotide sequence set forth in SEQ ID NO:1.

6. The transgenic plant of claim 1 wherein the marigold beta-cyclase comprises the amino acid sequence of SEQ ID NO:2.

7. A transgenic plant comprising an isolated DNA encoding marigold beta-cyclase and one or more isolated DNAs selected from the group consisting of a DNA encoding marigold beta-hydroxylase, a DNA encoding marigold IPP isomerase, and a DNA encoding marigold epsilon-cyclase.

8. The transgenic plant of claim 7 wherein the DNA encoding marigold beta-cyclase comprises the nucleotide sequence set forth in SEQ ID NO:1, the DNA encoding marigold beta-hydroxylase comprises the nucleotide sequence set forth in SEQ ID NO:3, the DNA encoding marigold epsilon-cyclase comprises the nucleotide sequence set forth in SEQ ID NO:5, and the DNA encoding marigold IPP isomerase comprises the nucleotide sequence set forth in SEQ ID NO:7.

9. The transgenic plant of claim 7 wherein the beta-hydroxylase comprises the amino acid sequence of SEQ ID NO:2, the beta-cyclase comprises the amino acid sequence of SEQ ID NO:4, the epsilon-cyclase comprises the amino acid sequence of SEQ ID NO:6, and the IPP isomerase comprises the amino acid sequence of SEQ ID NO:8.

10. A transgenic plant comprising an isolated DNA encoding marigold beta-cyclase, wherein said DNA is in the antisense orientation.

11. The transgenic plant of claim 10 wherein the isolated DNA comprises the nucleotide sequence set forth in SEQ ID NO;1.

12. The transgenic plant of claim 10 wherein the beta-cyclase comprises the amino acid sequence set forth in SEQ ID NO:2.

13. A transgenic plant comprising a marigold DNA sequence encoding beta-cyclase wherein the 5' end of the DNA sequence is operably linked to a promoter and the 3' end of the DNA sequence is operably linked to a regulatory sequence containing a polyadenylation signal.

14. A transgenic plant comprising in the antisense orientation a marigold DNA sequence encoding beta-cyclase wherein the 5' end of the DNA sequence is operably linked to a promoter and the 3' end of the DNA sequence is operably linked to a regulatory sequence containing a polyadenylation signal.

15. A transgenic plant comprising a marigold DNA sequence encoding beta-cyclase and at least one marigold DNA sequence selected from the group consisting of a DNA sequence encoding beta-hydroxylase, a DNA sequence encoding epsilon-cyclase and a DNA sequence encoding IPP isomerase, wherein the 5' end of each of the DNA sequences is operably linked to a promoter and the 3' end is operably linked to a regulatory sequence containing a polyadenylation signal, and wherein at least one DNA sequence is in the antisense orientation and the remaining DNA sequences are in the sense orientation.

16. The transgenic plant of claim 15, wherein the DNA sequence encoding beta-cyclase comprises the nucleotide sequence set forth in SEQ ID NO:1, the DNA sequence encoding beta-hydroxylase comprises the nucleotide sequence set forth in SEQ ID NO:3, the DNA sequence encoding IPP isomerase comprises the nucleotide sequence set forth in SEQ ID NO:7, and the DNA sequence encoding epsilon-cyclase comprises the nucleotide sequence set forth in SEQ ID NO:5.

17. The transgenic plant of claim 13 or 14 further comprising at least one marigold DNA sequence selected from the group consisting of a DNA sequence encoding beta-cyclase, a DNA sequence encoding beta-hydroxylase, a DNA sequence encoding epsilon-cyclase, and a DNA sequence encoding IPP isomerase, wherein the 5' end of each of the DNA sequences is operably linked to a promoter and the 3' end of each of the DNA sequences is operably linked to a regulatory sequence containing a polyadenylation signal.

18. The transgenic plant of claim 17 wherein the DNA sequence encoding beta-cyclase comprises the nucleotide sequence set forth in SEQ ID NO:1, the DNA sequence encoding beta-hydroxylase comprises the nucleotide sequence in SEQ ID NO:3, the DNA sequence encoding epsilon-cyclase comprises the nucleotide sequence in SEQ ID NO:5, and the DNA sequence encoding IPP isomerase comprises the nucleotide sequence in SEQ ID NO:7.

19. The transgenic plant of any one of claim 13, 14 or 15 wherein the promoter is a petal specific promoter.

20. The transgenic plant of any one of claim 13, 14 or 15 wherein the promoter is a promoter for a ketolase gene from *Adonis vernalis*.

* * * * *

UNITED STATES PATENT AND TRADEMARK OFFICE
CERTIFICATE OF CORRECTION

PATENT NO. : 6,232,530 B1
DATED : May 15, 2001
INVENTOR(S) : Dean DellaPenna, Francis X. Cunningham, Jr.

It is certified that error appears in the above-identified patent and that said Letters Patent is hereby corrected as shown below:

Column 45, claim 5,
Line 26, "Claim 1" should be -- Claim 4 --.

Column 45, claim 6,
Line 29, "Claim 1" should be -- Claim 4 --.

Signed and Sealed this

Twenty-seventh Day of November, 2001

*Attest:*

NICHOLAS P. GODICI
*Acting Director of the United States Patent and Trademark Office*

*Attesting Officer*